United States Patent
Pananen et al.

(10) Patent No.: US 11,944,786 B2
(45) Date of Patent: Apr. 2, 2024

(54) INFUSION DEVICE

(71) Applicant: Medtronic MiniMed, Inc., Northridge, CA (US)

(72) Inventors: Jacob E. Pananen, Agoura Hills, CA (US); Ellis Garai, Studio City, CA (US)

(73) Assignee: Medtronic MiniMed, Inc., Northridge, CA (US)

( * ) Notice: Subject to any disclaimer, the term of this patent is extended or adjusted under 35 U.S.C. 154(b) by 487 days.

(21) Appl. No.: 17/151,385

(22) Filed: Jan. 18, 2021

(65) Prior Publication Data

US 2022/0226573 A1 Jul. 21, 2022

(51) Int. Cl.
*A61M 5/172* (2006.01)
*A61M 5/142* (2006.01)
*A61M 5/158* (2006.01)

(52) U.S. Cl.
CPC ...... *A61M 5/1723* (2013.01); *A61M 5/14248* (2013.01); *A61M 2005/1583* (2013.01);
(Continued)

(58) Field of Classification Search
CPC ............ A61M 5/1723; A61M 5/14248; A61M 5/172; A61M 5/14244; A61M 5/142; A61M 5/14; A61M 5/158; A61M 5/162; A61M 2005/1583; A61M 2005/1585; A61M 2005/1726; A61M 2005/14268; A61M 2005/14252; A61M 2205/52; A61M 2205/33; A61M 2205/3303; A61M 2205/3327; A61M 2230/201; A61B 5/4839; A61B 5/145; A61B 5/14532;
(Continued)

(56) References Cited

U.S. PATENT DOCUMENTS 8,475,432 B2 * 7/2013 Moberg ............ A61M 5/14248
604/135
8,641,670 B2 2/2014 Yodfat et al.
(Continued)

FOREIGN PATENT DOCUMENTS

CA 3143537 A1 12/2020

OTHER PUBLICATIONS

U.S. Appl. No. 17/109,600, filed Dec. 2, 2020, naming inventors Pananen et al.
(Continued)

*Primary Examiner* — James D Ponton
*Assistant Examiner* — Sarah Dympna Grasmeder
(74) *Attorney, Agent, or Firm* — Fortem IP LLP; Mary L. Fox

(57) ABSTRACT

An infusion device configured to implant a cannula and a sensor in a user. The infusion device includes a first unit defining a first housing and a second unit defining a second housing. The second housing is configured to engage the first housing. The infusion device includes a first insertion needle configured to implant the cannula in the user and a second insertion needle configured to implant the sensor in the user when the second unit engages the first unit. The infusion device includes processing circuitry in electrical communication with the sensor and a fluid reservoir in fluid communication with the cannula. In examples, the first unit and the second unit are configured to engage using an inserter.

20 Claims, 9 Drawing Sheets

(52) U.S. Cl.
CPC . *A61M 2005/1585* (2013.01); *A61M 2205/52* (2013.01); *A61M 2205/8206* (2013.01); *A61M 2230/201* (2013.01)

(58) Field of Classification Search
CPC . A61B 5/4836; A61B 5/14503; A61B 5/6847; A61B 5/6848; A61B 5/1473; A61B 5/14865
See application file for complete search history.

(56) References Cited

U.S. PATENT DOCUMENTS

| | | | |
|---|---|---|---|
| 8,679,062 B2 | 3/2014 | Yodfat et al. | |
| 8,747,363 B2 | 6/2014 | Nielsen et al. | |
| 9,545,477 B2 | 1/2017 | Chong et al. | |
| 9,610,402 B2 | 4/2017 | Yavorsky et al. | |
| 9,839,747 B2 | 12/2017 | Smith et al. | |
| 9,943,643 B2 | 4/2018 | Constantineau et al. | |
| 9,943,653 B2 * | 4/2018 | Kamen | F04B 7/00 |
| 10,092,691 B2 | 10/2018 | Searle et al. | |
| 10,195,342 B2 | 2/2019 | Cole et al. | |
| 10,220,145 B2 | 3/2019 | Jennewine | |
| 10,413,183 B2 | 9/2019 | Antonio et al. | |
| 10,413,658 B2 | 9/2019 | Gillett et al. | |
| 10,441,717 B2 | 10/2019 | Schmid et al. | |
| 10,463,787 B2 | 11/2019 | Shor et al. | |
| 10,569,011 B2 | 2/2020 | Dilanni et al. | |
| 10,596,295 B2 | 3/2020 | Larson et al. | |
| 2006/0253085 A1 | 11/2006 | Geismar et al. | |
| 2007/0191702 A1 | 8/2007 | Yodfat et al. | |
| 2008/0051716 A1 | 2/2008 | Stutz | |
| 2009/0012472 A1 | 1/2009 | Ahm et al. | |
| 2009/0143660 A1 | 6/2009 | Brister et al. | |
| 2010/0076412 A1 | 3/2010 | Rush et al. | |
| 2015/0164545 A1 * | 6/2015 | Gyrn | A61B 17/3403 600/300 |
| 2017/0021137 A1 | 1/2017 | Cole | |
| 2017/0232191 A1 | 8/2017 | Smith et al. | |
| 2019/0160225 A1 | 5/2019 | Verlaak et al. | |
| 2020/0023122 A1 | 1/2020 | McCullough et al. | |
| 2020/0384193 A1 | 12/2020 | Chiu et al. | |

OTHER PUBLICATIONS

U.S. Appl. No. 17/150,368, filed Jan. 15, 2021, naming inventors Pananen et al.

U.S. Appl. No. 16/893,141, filed Jun. 4, 2020, naming inventors Chiu et al.

* cited by examiner

INFUSION DEVICE

TECHNICAL FIELD

This disclosure relates generally to systems for the insertion of medical devices.

BACKGROUND

Certain diseases or conditions may be treated, according to modern medical techniques, by delivering a medication fluid or other substance to the body of a patient, either in a continuous manner or at particular times or time intervals within an overall time period. For example, diabetes is often treated by delivering defined amounts of insulin to the patient at appropriate times. Some modern systems employ programmable fluid infusion devices (e.g., insulin pumps) to deliver controlled amounts of insulin to a patient. Some modes of providing insulin therapy to a user include delivery of insulin through manually operated syringes and insulin pens. Some other modes employ programmable fluid infusion devices (e.g., insulin pumps) to deliver controlled amounts of insulin to a user. Moreover, in certain instances, it may be desirable for a user to receive feedback from a physiological characteristic monitor, such as a glucose monitor. In these instances, the physiological characteristic monitor and the infusion set are often separately coupled to the user's anatomy at different insertion sites.

BRIEF SUMMARY

The disclosure generally relates to an infusion device configured to implant a cannula and a sensor within a user. The infusion device may be configured to be worn by the user. The infusion device may include a first unit configured to contact the skin of the user and a second unit configured to engage the first unit. The second unit includes a first insertion needle configured to implant the cannula and a second insertion needle to implant the sensor when the second unit engages the first unit. The infusion device is configured to fluidly connect the cannula with a fluid reservoir within the first unit and electrically connect the sensor with processing circuitry within the first unit engages the second unit. The first unit may be configured to substantially limit motion of the second unit relative to the first unit when the second unit engages the first unit.

The infusion device may be configured to withdraw the first and second insertion needles when the second unit is engaged with the first unit. The infusion device is configured such that the cannula and the sensor remain implanted when the insertion needles are withdrawn and the second unit engages the first unit. The second unit may be configured such that the cannula and the sensor withdraw from the user when the user disengages the second unit from the first unit. The infusion device is configured such that the second unit may be replaced as the first unit remains proximate the user.

In an example, an infusion device comprises: a first unit defining a first housing, wherein the first housing defines a first channel extending through the first housing, a second channel extending through the first housing, and a fluid access, wherein the first unit includes processing circuitry and a fluid reservoir in fluid communication with the fluid access; and a second unit defining an second housing configured to engage the first housing, the second unit comprising: a cannula having a first end and a second end; and a sensor; a first insertion needle releasably carrying the cannula; and a second insertion needle releasably carrying the sensor, wherein: the first insertion needle is configured to insert the first end of the cannula through the first channel when the second housing engages the first housing, the second insertion needle is configured to insert the sensor through the second channel when the second housing engages the first housing, the second end of the cannula is configured to insert through the fluid access when the second housing engages the first housing, and the infusion device is configured to electrically connect the sensor and the processing circuitry when the second housing engages the first housing.

In an example, an infusion device comprises: a first unit defining a first housing, wherein the first housing defines a first channel extending through the first housing, a second channel extending through the first housing, and a fluid access, and wherein the first unit includes processing circuitry, a fluid reservoir, and a fluid pump in fluid communication with the fluid access; and a second unit defining an second housing configured to engage the first housing, the second unit comprising: a cannula having a first end and a second end; and a sensor; a first insertion needle releasably carrying the cannula and configured to extend through the first channel; and a second insertion needle releasably carrying the sensor and configured to extend through the second channel, wherein: the first housing is configured to substantially secure the second housing from movement relative to the first housing when the second housing engages the first housing, the first insertion needle is configured to extend a portion of the cannula including the first end through the first channel when the first insertion needle extends through the first channel, the second insertion needle is configured to extend a portion of the sensor through the second channel when the second insertion needle extends through the second channel, the second end of the cannula is configured to insert through the fluid access when the second housing engages the first housing, wherein the cannula is configured to establish fluid communication from the first end of the cannula to the fluid reservoir when the second end of the cannula inserts through the fluid access, and the infusion device is configured to electrically connect the sensor and the processing circuitry when the second housing engages the first housing.

In an example, a technique includes: engaging a first housing defined by a first unit and a second housing defined by a second unit, wherein the first unit includes processing circuitry and a fluid reservoir, and wherein the second unit includes a first insertion needle, a second insertion needle, a cannula, and a sensor; inserting, when the second housing engages the first housing, a first end of the cannula through a first channel defined by the first housing using the first insertion needle; inserting, when the second housing engages the first housing, the sensor through a second channel defined by the first housing using the second insertion needle; inserting, when the second housing engages the first housing, a second end of the cannula into a fluid access defined by the first housing; and electrically connecting, when the second housing engages the first housing, the sensor and the processing circuitry.

The details of one or more examples are set forth in the accompanying drawings and the description below. Other features, objects, and advantages will be apparent from the description and drawings, and from the claims.

DETAILED DESCRIPTION

Figure 1:
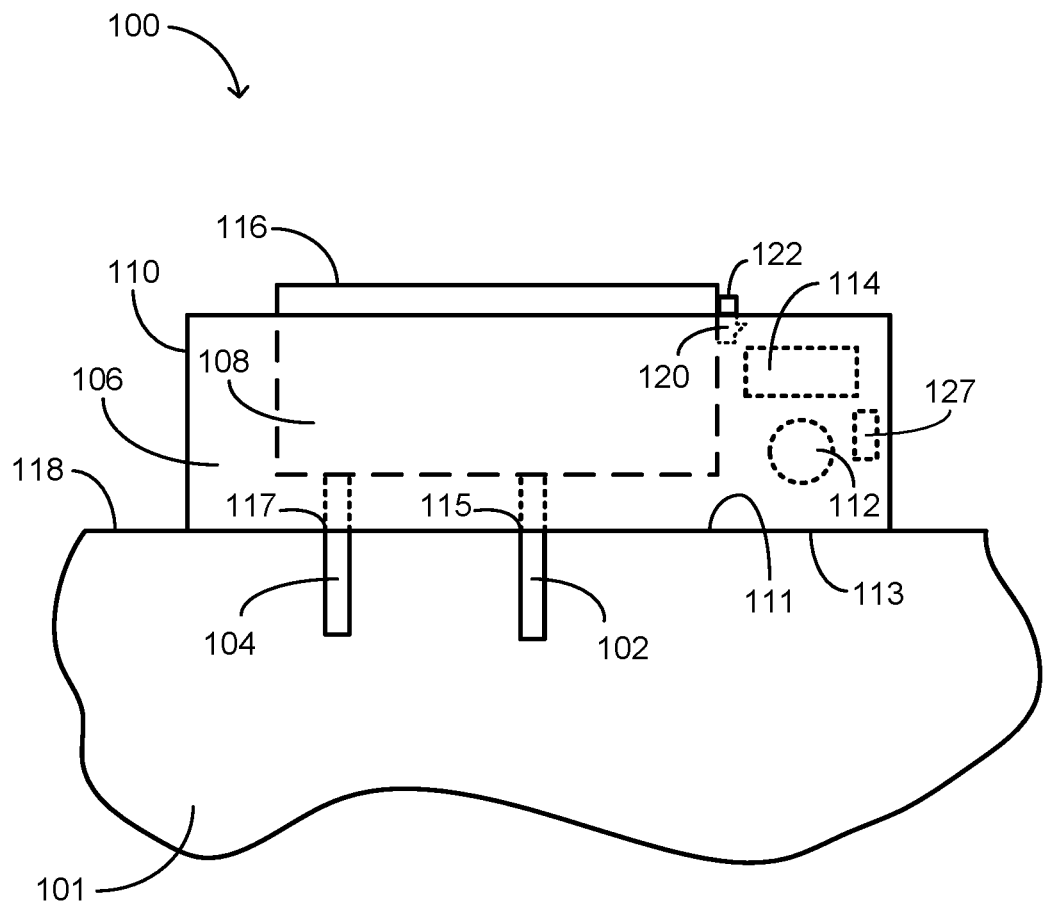
FIG. 1 is a schematic view of an infusion device attached to the body of a user.

The disclosure describes an infusion device configured to implant a cannula and a sensor within a user. The infusion device may be generally related to a fluid infusion device configured to provide a therapeutic fluid to a user and monitor a physiological characteristic of the user. For example, the cannula may be a fluid delivery cannula configured to deliver a fluid (e.g., insulin) to the user. The sensor may be an analyte sensor (e.g., a glucose sensor) configured to detect a physiological characteristic of the user (e.g., a glucose level). The infusion device may be configured to implant the cannula and the sensor in the user substantially concurrently but the examples are not limited to substantially concurrent implantation of the cannula and sensor. In examples, the infusion device is a portable system configured to be worn by the user.

The infusion device includes a first unit configured to engage a second unit. The first unit and the second unit may be substantially separate units. For example, the first unit may include one or more components mechanically supported and/or housed substantially within a first housing and the second unit may include one or more components mechanically supported and/or housed substantially within a second housing. The second unit (e.g., the second housing) may be configured to engage the first unit (e.g., the first housing) such that the components of the first unit and second unit cooperatively operate for therapeutic benefit to a user.

In examples, the infusion device is configured such that the second unit may be engaged with (e.g., installed on) and/or disengaged from (e.g., separated) from the first unit through actions of the user. For example, the user may install the second unit on the first unit to initiate use of the cannula, sensor, and other components of the infusion device. The user may separate the second unit and the first unit subsequent to the use. In examples, the first unit is configured to position on the user (e.g., on the skin of the user), and the second unit may be installed and removed as the first unit is positioned on the user. The second unit may be substantially replaceable, such that a particular second unit initially installed on the first unit may be removed by the user and replaced with another similar and/or largely identical second unit. In some examples, the infusion device is configured such that second unit may be replaced as the first unit remains positioned on the user.

The first unit may be configured to limit movement of the second unit relative to the first unit when the second unit engages the first unit. In examples, the second housing of the second unit is configured to engage (e.g., mechanically engage) the first housing of the first unit to limit movement of the second housing relative to the first housing. The second housing may be configured to engage the first housing such that components of the first unit and components of the second unit cooperatively operate to provide a therapeutic fluid (e.g., insulin) to the user using the cannula and monitor a physiological characteristic of the user (e.g., a glucose level) using the sensor.

The infusion device may be configured to implant the cannula and the sensor within the user. In examples, the infusion device is configured to implant the cannula and the sensor during the installation of the second unit on the first unit. The second unit may include a first insertion needle configured to implant the cannula and a second insertion needle configured to implant the sensor. The first insertion needle and the second insertion needle may releasably carry the cannula and the sensor respectively. The infusion device may be configured to cause the implantation of the cannula and the sensor within the user as the second unit engages or is caused to engage the first unit. For example, the infusion device may be configured such that, as the second unit engages the first unit (e.g., by the user), the first insertion needle and the second insertion needle extend from the infusion device to cause the implantation.

In examples, the cannula is an insulin cannula and the sensor is a glucose sensor. Including both the glucose sensor and the insulin cannula within the infusion device (e.g., in the first unit) may allows for a "closed loop" system whereby insulin delivery to the user may be adjusted in real-time based on readings from the glucose sensor. Such real-time adjustment may assist in maintaining the user's glucose levels. Further, this may reduce a need for the user to carry separate insulin infusion and glucose monitoring devices. Including both an insulin cannula and glucose sensor may provide for an infusion device that is more convenient for a user to carry, and may reduce/and/or limit the number of insertion sites required.

In examples, the infusion device is configured to implant the cannula and the sensor when the first unit is positioned on the user (e.g., on the skin of the user). The first insertion needle and second insertion needle may be configured to extend from the second unit and pass through the first unit to cause the implantation as the second unit engages the first unit, such that distal ends of the first insertion needle and the second insertion needle pierce the skin of the user. In examples, the infusion device is configured such the first housing of the first unit is between the second housing of the second unit and the user when the first insertion needle and the second insertion needle cause the implantation. The infusion device may be configured such that, when the first unit is positioned on the user, movement of the second unit in a first direction toward the first unit causes the first insertion needle and the second insertion needle to extend through the first unit to implant the cannula and the sensor. The movement in the first direction (e.g., toward the user) may cause the second housing of the second unit to engage the first housing of the first unit, such that the first housing limits and/or substantially prevents movement of the second housing relative to the first housing.

In examples, the infusion device is configured such that the first insertion needle and the second insertion needle pierce the skin of the user substantially concurrently. The infusion device may be configured to cause the first insertion needle and the second insertion needle to pierce the skin of the user substantially concurrently as the second unit is caused to engage the first unit (e.g., caused by the user). The infusion device may cause the first insertion needle and the second insertion needle to insert substantially concurrently in order to, for example, limit discomfort to the user that might be caused by insertions separated by a user-discernable chronological time increment. In other examples, the infusion device may be configured to cause the first insertion needle and the second insertion needle to insert at substantially different chronological time increments.

The infusion device may be configured such that the first insertion needle and/or the second insertion needle may be withdrawn in a second direction (e.g., away from the user) substantially opposite the first direction as the second housing remains engaged with the first housing, such that the first insertion needle and/or the second insertion needle may be withdrawn from the user as the second unit remains positioned on the first unit. The first insertion needle may be configured to release the cannula as the first insertion needle is withdrawn in the second direction. The second insertion needle may be configured to release the sensor as the second insertion needle is withdrawn in the second direction.

Hence, the infusion device may be configured such that the user may cause the implantation of the cannula and the sensor by causing the second unit to engage the first unit. The infusion device may be configured such that the user may cause the withdrawal of the first insertion needle and/or the second insertion needle following the implantations. In examples, the infusion device is configured such that the first insertion needle and/or the second insertion needle are substantially separable from the first unit and the second unit when the first insertion needle and/or the second insertion needle are withdrawn in the second direction (e.g., away from the user), such that user may continue to utilize the functions of the first unit and the second unit without the continued presence of the first insertion needle and/or the second insertion needle.

In examples, the first unit includes a fluid reservoir configured to hold a fluid and processing circuitry configured to communicate with a sensor. The second unit may include the cannula and the sensor. The infusion device may be configured such that, when the second housing engages the first housing, the cannula of the second unit is placed in fluid communication with the fluid reservoir of the first unit to allow the infusion device to supply the therapeutic fluid. The infusion device may be configured such that, when the second housing engages the first housing, the processing circuitry is placed in electrical communication with the sensor, such that the sensor may communicate with the processing circuitry. In examples, the infusion device includes a fluid pump (e.g., an insulin pump) configured to deliver the therapeutic fluid from the fluid reservoir to the cannula, and the processing circuitry is configured to control an operation of the fluid pump (e.g., to commence or cease pumping) based on a signal from the sensor.

The second unit is configured to support the cannula such that cannula establishes fluid communication with the fluid reservoir of the first unit when the second housing is engaged with the first housing. In examples, the cannula includes a lumen configured to establish fluid communication between a first end of the cannula ("cannula first end") and a second end of the cannula ("cannula second end") opposite the cannula first end. In examples, the second unit mechanically supports a portion of the cannula including the cannula second end such that, when the second housing engages the first housing, the cannula second end inserts into the fluid access of the first unit. The first insertion needle may be configured to implant the cannula first end in the user as the second housing engages the first housing. Thus, the second unit may be configured such that the cannula establishes fluid communication between the fluid reservoir of the first unit and the cannula first end implanted in the user when the second housing engages the first housing. In examples, the cannula second end is configured to pierce a septum providing fluid isolation between the fluid reservoir and the first housing of the first unit to establish the fluid communication.

The infusion device is configured to establish communication between the sensor of the second unit and the processing circuitry of the first unit when the second housing engages the first housing. In examples, the first unit includes a first connector in electrical communication with the processing circuitry and the second unit includes a second connector in electrical communication with the sensor. The infusion device is configured such that engagement of the second housing with the first housing causes the second connector to establish an electrical connection with the first connector, such that the sensor (in the second unit) may provide a signal to the processing circuitry (in the first unit) indicative of a physiological characteristic of the user (e.g., a glucose level). The infusion device may be configured such that when the second end of the cannula inserts into the fluid access (e.g., when the second unit engages the first unit), the second connector establishes the electrical connection with the first connector. In examples, the second unit is configured to mechanically support the second electrical connector and the cannula such that engagement of the second unit and the first unit causes the second end of the cannula to insert into the fluid access and the second connector to establish the electrical connection with the first connector.

The first unit may be configured such that the first insertion needle and/or the second insertion needle are translatable relative to the first unit. The first insertion needle may be translatable through the first unit in a distal direction ("first needle distal direction") and in a proximal direction ("first needle proximal direction) opposite the first needle distal direction. The first needle may be configured to translate in the first needle distal direction to pierce the skin of the user, and to translate in the first needle proximal direction to withdraw from the skin of the user.

In examples, the second unit is configured such that the first insertion needle and/or the second insertion needle is translatable relative to the second unit. For example, the second unit may be configured such that the first insertion needle and/or second insertion needle translates relative to the second unit in order to withdraw the first insertion needle and/or the second insertion needle from the user as the second housing remains engaged with the first housing. In examples, the infusion device is configured such that the first insertion needle may extend and/or translate through the first unit concurrent with extending through the second unit.

The infusion device may be configured to substantially the second unit and the first unit such that the first insertion needle may pass through the second unit and the first unit when the engagement of the second housing and the first housing causes the second end of the cannula to insert into the fluid access. The infusion device may be configured to substantially the second unit and the first unit such that the first insertion needle may pass through the second unit and the first unit when the engagement of the second housing and the first housing causes the second connector to establish the electrical connection with the first connector.

In examples, the infusion device includes an inserter configured to cause the second housing of the second unit to engage the first housing of the first unit. The inserter may be configured to hold the second unit is a disengaged position wherein the second unit is displaced from the first unit, and configured to cause the second unit to move to an engaged position wherein the second housing engages the first housing. In examples, the inserter is configured to mate with the first unit when the inserter holds the second unit in the disengaged position. The inserter may be configured to substantially align the second unit and the first unit, such that when the inserter causes the engagement of the second housing and the first housing, the components of the first unit and second unit may cooperatively operate to provide a therapeutic fluid (e.g., insulin) to the user using the cannula and monitor a physiological characteristic of the user (e.g., a glucose level) using the sensor.

In examples, the inserter is configured such that a user may cause the inserter to move the second unit from the disengaged position to the engaged position. In examples, the inserter is configured to cause the first insertion needle to implant the cannula and the second insertion needle to implant the sensor into the user when the inserter moves the second unit from the disengaged position to the engaged position. The inserter may include a user input device configured to cause the inserter to move the second unit from the disengaged position to the engaged position, such that the user may control the implantation of the cannula and the sensor. The user input device may be, for example, a button on the inserter, a wireless communication device, or some other user-controlled activation device. In some examples, the inserter is configured such that a force imparted by the user on the inserter (e.g., a force toward the skin of the user) causes the inserter to move the second device from the disengaged position to the engaged position. The inserter may be configured such that, when the inserter moves the second device from the disengaged position to the engaged position, the first insertion needle moves in the first distal direction through the first housing and the second insertion needle moves in the second distal direction through the first housing to pierce the skin of the user and implant the cannula and the sensor respectively.

The inserter may be configured to align the second electrical connector of the second unit with the first electrical connector of the first unit when the inserter mates with the first unit, such that the second electrical connector establishes the electrical connection with the first electrical connector when the inserter moves the second unit from the disengaged position to the engaged position. In examples, the inserter is configured to align the second end of the cannula of the second unit with the fluid access of the first unit when the inserter mates with the first unit, such that the second end of the cannula inserts in the fluid access when the inserter moves the second unit from the disengaged position to the engaged position. The inserter may be configured to align the second unit first channel with the first unit first channel when the inserter mates with the first unit, such that the first insertion needle may extend through the second unit first channel and the first unit first channel when the inserter moves the second unit to the engaged position. The inserter may be configured to align the second unit second channel with the first unit second channel when the inserter mates with the first unit, such that the second insertion needle may extend through the second unit second channel and the first unit second channel when the inserter moves the second unit to the engaged position.

The inserter may be configured to withdraw the first insertion needle and/or the second insertion needle from the user when the cannula and the sensor are implanted. The inserter may withdraw the first insertion needle and/or the second insertion needle as the second housing remains engaged with the first housing. In examples, the inserter is configured to cause an initial insertion of the first insertion needle and the second insertion needle followed by a subsequent withdrawal of the first insertion needle and the second insertion needle in response to a single actuation of the inserter by the user. The inserter may be configured to initially cause the first insertion needle and/or the second insertion needle to extend in a distal direction by a certain amount to implant the cannula and the sensor, then subsequently cause the first insertion needle and/or the second insertion needle to withdraw in a proximal direction to withdraw from the skin of the user. The inserter may be configured to withdraw the first insertion needle and the second insertion from the first unit and the second unit as the first housing remains engaged with the second housing and the cannula and the sensor remain implanted in the user.

The infusion device may be configured to be positioned proximate to the skin of the user. In examples, the first housing is configured to contact the skin of the user. The infusion device may be configured to substantially secure its location on the user in order to, for example, allow mobility to the user as the infusion device administers and monitors therapies delivered to the user. For example, the infusion device may be configured to allow a degree of user mobility as the infusion device delivers insulin to the user through the cannula and monitors a glucose level of the user using the sensor. The infusion device may be substantially secured to the user using any suitable arrangement. In some examples, the first housing and/or second housing of the infusion device includes an adhesive element configured to removably secure the infusion device to the skin of the user. The infusion device may be utilized to administer a variety of medications to a user such as, but not limited to, disease treatments, drugs to treat pulmonary hypertension, iron chelation drugs, pain medications, anti-cancer treatments, medications, vitamins, hormones, and the like.

FIG. 1 is a schematic view of portions of an infusion device 100 contacting a body 101 of a user. In FIG. 1, infusion device 100 is implemented as a fluid infusion device configured to provide a therapeutic fluid to the user and monitor a physiological characteristic of the user. Infusion device 100 includes a cannula 102 and a sensor 104. Cannula 102 is implanted in body 101 and configured to deliver a fluid (e.g., insulin) to the body 101. Sensor 104 (e.g., a glucose sensor) is implanted in body 101 and configured to detect a physiological characteristic of the user (e.g., a glucose level).

Infusion device 100 includes a first unit 106 and a second unit 108. First unit 106 includes a first housing 110 mechanically supporting one or more components of first unit 106, such as fluid reservoir 112 and processing circuitry 114. Second unit 108 includes second housing 116 mechanically supporting one or more components of second unit 104, such as cannula 102 and sensor 104. Second unit 108 engages (e.g., mechanically engages) first unit 106 such that components of second unit 108 and components of first unit 106 cooperatively operate to provide a therapeutic fluid (e.g., insulin) to the user using cannula 102 and monitor a physiological characteristic of the user (e.g., a glucose level) using sensor 104. Portions of first unit 106 and second unit 108 are depicted as hidden using dashed lines in FIG. 1.

Infusion device 100 may be configured such that first unit 106 and second unit 108 define substantially separable units. Infusion device 100 may be configured such that second unit 108 may be engaged with (e.g., installed on) and/or disengaged from (e.g., separated) from first unit 106 through actions of the user, or by some other actions. For example, the user may install second unit 108 on first unit 106 prior to use. In examples, second unit 108 may be caused to engage first unit 106 using an inserter (not shown) configured to be operated by the user. The user may separate second unit 108 and first unit 106 subsequent to the use. In examples, first unit 106 is configured to position on the user (e.g., on skin 118 of body 101 of the user), and second unit 108 may be installed and removed as first unit 106 remains positioned on the user. Second unit 108 may be substantially replaceable, such that the particular second unit 108 depicted in FIG. 1 may be removed by the user and substituted with a replacement second unit (not shown) configured similarly and/or largely identically to second unit 108.

Infusion device 100 may be configured such that disengagement and separation of second unit 108 from first unit 106 withdraws cannula 102 and sensor 104 from body 101 of the user, allowing for disposal of cannula 102 and sensor 104 following use. Infusion device 100 may be configured such that a cannula and sensor of the replacement second unit implants within the body 101 when the replacement second unit is substituted for second unit 108. As will be discussed, second unit 108 may include a first insertion needle (not shown) and a second insertion needle (not shown) configured to implant cannula 102 and sensor 104 in body 101 when second unit 108 engages first unit 106. The first insertion needle and second insertion needle may be withdrawn and substantially displaced from second unit 108 and first unit 106 following the implantation to, for example, improve the comfort of the user when infusion device 100 is worn as a portable device.

First unit 106 may be configured to limit movement of second unit 108 when second unit 108 and first unit 106 are engaged. In examples, second housing 116 is configured to engage (e.g., mechanically engage) first housing 110 to limit movement of second housing 116 relative to first housing 110. In examples, second housing 116 or first housing 110 defines a fixation device 120 configured to limit movement of second housing 116 relative to first housing 110 when second housing 116 engages first housing 110. Fixation device 120 may be, for example, a mechanical structure configured to substantially secure second housing 116 in a position relative to first housing 110, a magnetic or electromagnetic device configured to substantially secure second housing 116 in a position relative to first housing 110, or some other device configured to limit movement of second housing 116 relative to first housing 110. In some examples, fixation device 120 is configured to substantially secure second housing 116 relative to first housing 110 when second housing 116 is caused to engage first housing 110 (e.g., by the user). Fixation device 120 may be substantially affixed to either first housing 110 or second housing 116. That is, when second unit 108 is disengaged and displaced from first unit 106, fixation device 120 may be configured to remain affixed to either first unit 106 or second unit 108.

In examples, fixation device 120 is configured to establish at least a first position wherein fixation device 120 limits movement of second housing 116 relative to first housing 110 and at least a second position wherein fixation device 120 allows substantially independent movement of second housing 116 relative to first housing 110 (e.g., such that second unit 108 may be removed from first unit 106). Infusion device 100 may include a input device 122 configured to cause fixation device 120 to transition from the first position to the second position, or vice-versa. Input device 122 may be configured to be actuated by the user as needed to, for example, separate second unit 108 from first unit 106 when the unit desires to replace second unit 108. In examples, input device 122 is a manually operated button on first unit 106 and/or second unit 108, a circuitry configured to receive a communication (e.g., a wireless communication) from a smart phone, tablet, or other device, or some other device configured for control by the user.

In examples, input device 122 is a multipurpose input device configured to prompt multiple operations of infusion device 100. For example, input device 122 may be configured to cause one or more of the following functions, without limitation: waking up a processor and/or electronics of infusion device 100; configuring one or more settings of infusion device 100; initiating delivery of medication fluid; initiating a fluid priming operation; disabling alerts or alarms generated by infusion device 100; and the like. In lieu of a button, input device 122 can employ a slider mechanism, a pin, a lever, a switch, a touch-sensitive element, or the like. Input device 108 may be configured to receive a communication from a device remote from first housing 110 and/or second housing 116 (e.g., a wireless communication) to initiate to cause infusion device 100 to perform one or more of the described functions, or other functions. Infusion device 100 may include more than one input device 122 (e.g., more than one button) to initiate the various functions described.

Second housing 116 is configured to engage first housing 110 (e.g., via fixation device 120) such that components of first unit 106 and components of second unit 108 cooperatively operate to provide a therapeutic fluid (e.g., insulin) to the user using cannula 102 and monitor a physiological characteristic of the user (e.g., a glucose level) using sensor 104. In examples, first unit 106 includes fluid reservoir 112 configured to hold a fluid and processing circuitry 114 configured to communicate with a sensor. Second unit 108 may include cannula 102 and sensor 104. Infusion device 100 may be configured such that, when second housing 116 is engaged with first housing 110 (e.g., when second unit 108 is installed on first unit 106), cannula 102 of second unit 108 is placed in fluid communication with fluid reservoir 112 of first unit 106 to supply the therapeutic fluid. Infusion device 100 may be configured such that, when second housing 116 is engaged with first housing 110, processing circuitry 114 is placed in electrical communication with sensor 104, such that sensor 104 may communicate with processing circuitry 114. In examples, infusion device 100 includes a fluid pump 127 configured to deliver fluid from fluid reservoir 112 to cannula 102, and processing circuitry 114 is configured to control an operation of the fluid pump 127 (e.g., to commence or cease pumping) based on a signal from sensor 104. Thus, infusion device 100 is configured to cause the components of first unit 106 and the components of second unit 108 to cooperatively operate for therapeutic benefit to the user when second unit 108 is engaged with (e.g., installed on) first unit 106.

In examples, sensor 104 is configured to sense a physiological characteristic of a user. In some examples, sensor 104 is an glucose sensor. For example, sensor 104 may be an electrochemical sensor that includes the glucose oxidase enzyme. The glucose oxidase enzyme may enable sensor 104 to monitor glucose levels in a diabetic patient or user by affecting a reaction of glucose and oxygen. In some examples, sensor 104 includes a working electrode, a counter electrode, and a reference electrode. The working electrode may be coated with the glucose oxidase enzyme. The reference electrode may be configured to maintain a constant voltage to support a reaction at working electrode. The counter electrode may be configured to supply current to maintain the set potential on the working electrode. The working electrode, counter electrode and reference electrode may each be composed of a suitable biocompatible metal or metal alloy, such as copper, platinum, platinum-iridium, silver, gold, etc., and may be extruded. When glucose and oxygen diffuse to the glucose oxidase layer, hydrogen peroxide is formed. Hydrogen peroxide present at the working electrode metallization layer breaks down and generates electrons when a voltage is applied to the working electrode. In examples, sensor 104 is configured such that these electrons generates an electrical signal, which is transmitted by the working electrode and communicated to the processing circuitry of infusion device 100.

In examples, cannula 102 is substantially affixed to second unit 108, such that when second unit 108 is disengaged and displaced from first unit 106 (e.g., due to replacement of second unit 108 by a user), the separation of second unit 108 from first unit 106 causes cannula 102 to withdraw from body 101 of the user. Sensor 104 may be substantially affixed to second unit 108, such that when second unit 108 is disengaged and displaced from first unit 106, the separation of second unit 108 from first unit 106 causes sensor 104 to withdraw from body 101 of the user. Hence, infusion device 100 may be configured such that disengagement and separation of second unit 108 from first unit 106 withdraws cannula 102 and sensor 104 from body 101 of the user, allowing for disposal of cannula 102 and sensor 104 following use.

In examples, infusion device 100 is a portable device. Infusion device 100 may be a wearable device configured to be worn by the user. In examples, first housing 110 defines a base surface 111 configured to position proximate the skin 118 of the user. Base surface 111 may be configured to serve as the user-mounting structure of infusion device 100. Infusion device 100 may include an adhesive element 113 configured to substantially affix first housing 110 to the body of the user. In examples, adhesive element 113 may be located on base surface 111 of the first housing 110 such that first housing 110 can be temporarily adhered to the skin 118 of the user. Adhesive element 113 may cover substantially all of base surface 111, or may only partially cover base surface 111 if so desired. Adhesive element 113 may be, for example, a piece of double sided adhesive tape that is cut into the desired shape and size. In some examples, infusion device 100 is manufactured with an adhesive liner overlying adhesive element 113, and the adhesive liner is peeled away to expose the sticky surface of adhesive element 113.

In examples, base surface 111 defines a first hole 115 forming an opening through first housing 110. First hole 115 may be defined to accommodate passage of a first insertion needle (not shown) and at least a portion of cannula 102 from a position within first housing 110 to a position outside of first housing 110. First hole 115 may be configured to accommodate retraction of the first insertion needle from a position outside first housing 110 to a position within first housing 110 (e.g., during withdrawal of the first insertion needle). Base surface 111 may define at least a second hole 117 forming an opening through first housing 110. Second hole 117 may be defined to accommodate passage of a second insertion needle (not shown) and at least a portion of sensor 104 from a position within first housing 110 to a position outside of first housing 110. Second hole 117 may be configured to accommodate retraction of the second insertion needle from a position outside first housing 110 to a position within first housing 110 (e.g., during withdrawal of the second insertion needle).

Figure 2:
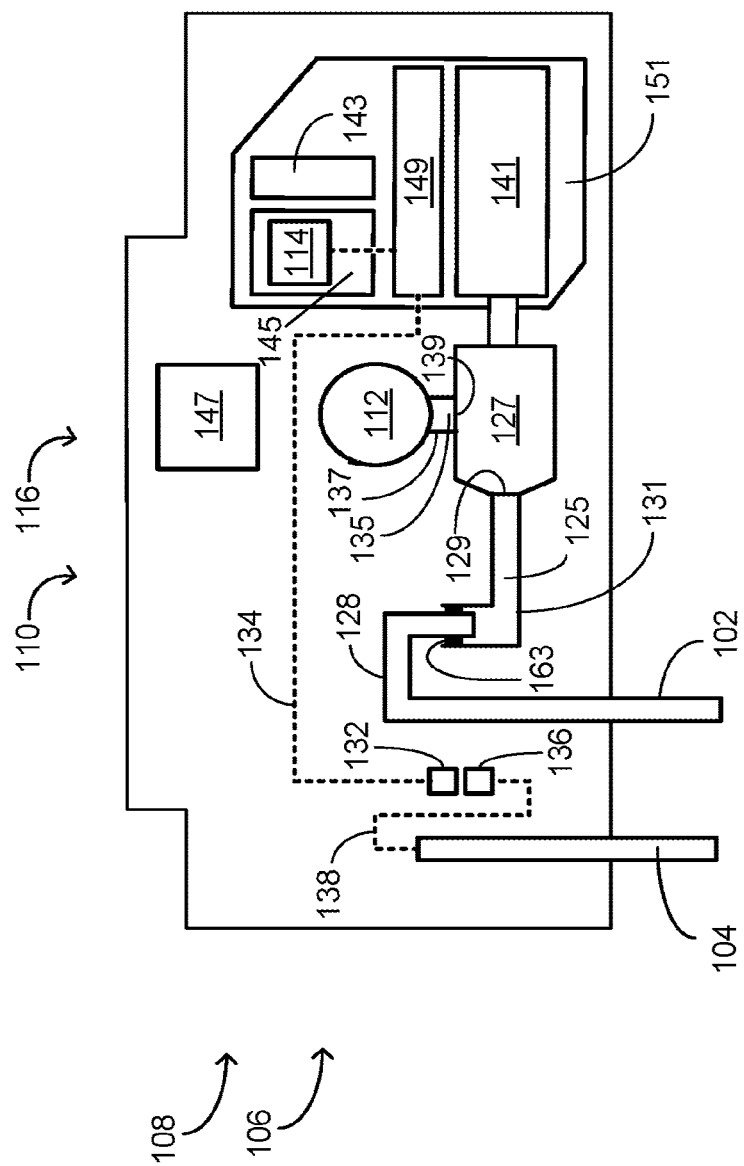
FIG. 2 is a simplified block diagram representation of an infusion device.

FIG. 2 depicts an example simplified block diagram representation of infusion device 100 with second housing 116 engaged with first housing 110. Infusion device 100 includes cannula 102, sensor 104, first unit 106 defining first housing 110, second unit 108 defining second housing 116, fluid reservoir 112, and processing circuitry 114. Infusion device 100 is configured to provide a fluid from fluid reservoir 112 to cannula 102 for the delivery of a fluid (e.g., insulin) to a user. Infusion device 100 is configured to monitor a physiological characteristic of the user using sensor 104.

Infusion device 100 is configured to define a first flow path 125 configured to provide a fluid (e.g., insulin) from fluid reservoir 112 to cannula 102 when second housing 116 engages first housing 110. Infusion device 100 may include fluid pump 127 (e.g., an insulin pump) configured to provide the fluid to cannula 102. In examples, infusion device 100 is configured to define first flow path 125 from a discharge 129 of fluid pump 127 through a lumen 128 of the cannula 102. In examples, infusion device 100 includes a first conduit 131 configured to define first flow path 125. In examples, infusion device 100 includes an access septum 163 configured to provide a fluid connection between flow path 125 and cannula 102. Infusion device 100 may be configured such that cannula 102 punctures through access septum 163 to place cannula 102 in fluid communication with flow path 125. Infusion device 100 may be configured to define a second flow path 135 from fluid reservoir 112 to a suction 137 of fluid pump 127. In examples, infusion device 100 includes a second conduit 139 configured to define second flow path 135. Fluid pump 127 may include motor 141 configured to cause fluid pump 127 to create pressure to deliver fluid (e.g., via first flow path 125). In some examples. Fluid pump 127 includes a piston and motor 141 is configured to cause translation of the piston. The piston may be configured to cause motivation of a fluid (e.g., insulin) through flow path 125 when motor 141 causes the translation. In some examples, the piston may be configured to reside in a reservoir filled with the fluid. The motor 141 may be a brushless DC motor, a brushed DC motor, or some other type of motor. In examples, motor 141 is powered and/or controlled by processing circuitry 114.

Infusion device 100 is configured to establish electrical connectivity between sensor 104 and processing circuitry 114 when second housing 116 engages first housing 110. Infusion device 100 may include a first connector 132 in electrical communication with processing circuitry 114 (e.g., via communication link 134) and a second connector 136 in electrical communication with sensor 104 (e.g., via communication link 138). In examples, first unit 106 includes first connector 132 and second unit 108 includes second connector 136. Infusion device 100 is configured to establish electrical connectivity between first connector 132 and second connector 136 when second housing 116 is engaged with first housing 110, such that sensor 104 is electrically connected to processing circuitry 114.

Infusion device 100 may include one or more of a processor device 143; a memory element 145 to store data, processor-readable program instructions, and the like; a battery 147 or other power source; and a sensor interface 149 configured to receive a signal from sensor 104. In examples, sensor interface 149 is configured to provide a signal indicative of a physiological parameter (e.g., a glucose level) to processing circuitry 114. In examples, sensor interface 104 is configured to measure a current from sensor 104. Sensor 104 may include hardware enabling measurement of the current, such as a potentiometer. In examples, processor device 143, sensor interface 104, and/or other components of infusion device 100 may be configured to conduct electrochemical impedance (EIS) measurements to determine, for example, a glucose level. Processor device 143, memory element 145, battery 147, and/or sensor interface 149 may be included on an electronics assembly 151. In examples, sensor interface 149 is configured to establish electrical connectivity between conductors of sensor 104 and conductors of electronics assembly 151. Electronics assembly 151 (or the components of electronics assembly 151) can be electrically coupled to other elements of infusion device 100 as needed to support the operation of infusion device 100. The electrical connections to electronics assembly 151 can be direct or indirect if so desired. Moreover, one or more components of electronics assembly 151 may support wireless data communication in some embodiments.

In examples, processor device 143 includes processing circuitry 114. In examples, processing circuitry 114 is configured to control an operation of fluid pump 127. For example, processing circuitry 114 may be configured to cause fluid pump 127 to commence, continue, and/or cease transporting fluid from fluid reservoir 112 to cannula 102. In examples, sensor 104 is configured to generate a signal indicative of a physiological characteristic of the user (e.g., a glucose level), and processing circuitry 114 is configured to determine the physiological characteristic using the indicative signal. In some examples, processing circuitry 114 is configured to control an operation of fluid pump 127 based on the indicative signal reported by the sensor 104.

First housing 110 of first unit 106 and second housing 116 of second unit 108 are suitably shaped, sized, and configured to house or support fluid pump 127, first conduit 131, second conduit 139, motor 141, processor device 143, memory element 145, battery 147, sensor interface 149, electronics assembly 151, and/or other components of infusion device 100 described. In examples, first unit 106 includes fluid reservoir 112, processing circuitry 114, fluid pump 127, first conduit 131, first connector 132, communication link 134, second conduit 139, motor 141, processor device 143, memory element 145, and/or battery 147. In examples, second unit 108 includes cannula 102, sensor 104, second connector 136 and/or communication link 134.

Figure 3:
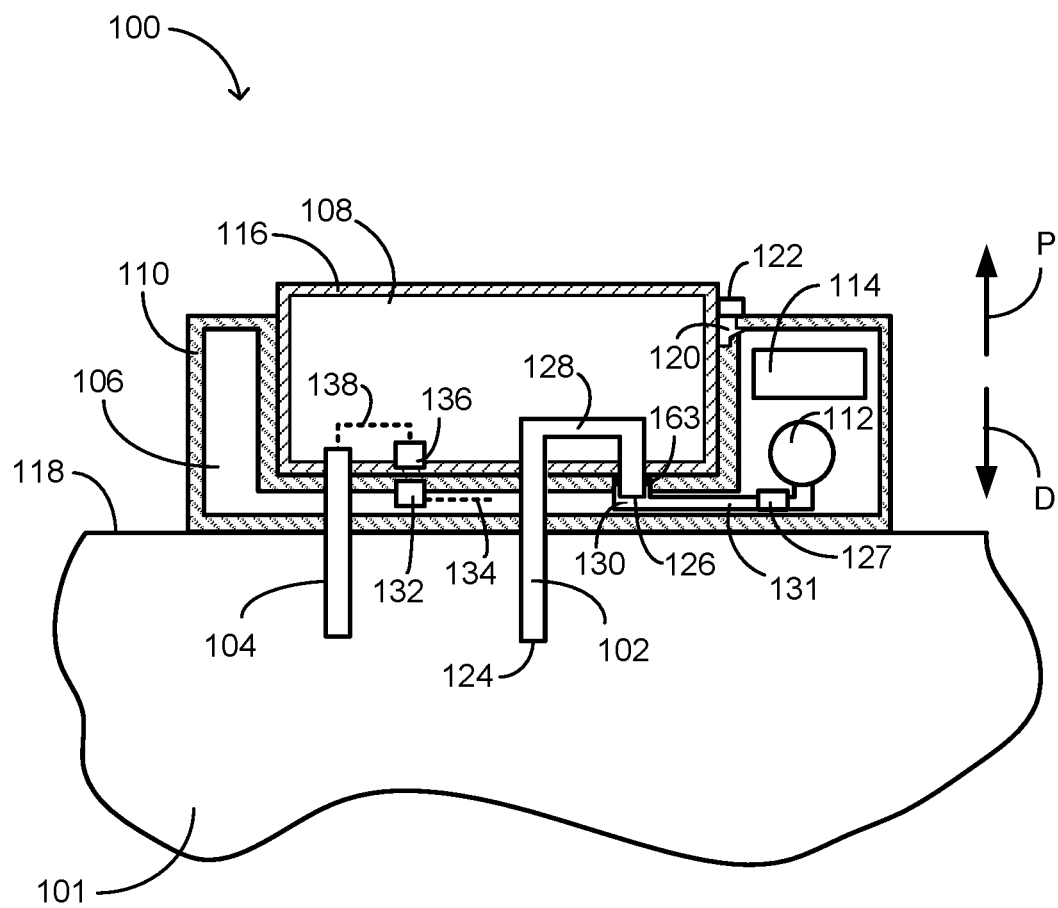
FIG. 3 is a schematic side view of an infusion device attached to the body of a user.

FIG. 3 is a schematic view of infusion device 100 including cannula 102, sensor 104, first unit 106 defining first housing 110, second unit 108 defining second housing 116, fluid reservoir 112, processing circuitry 114, fixation device 120, input device 122, and fluid pump 127. FIG. 3. Depicts example configurations of selected components within first unit 106 and second unit 108 when second unit 108 is engaged with first unit 106. First housing 110 and second housing 116 are illustrated as cross-sections with a cutting plane parallel to the page.

Second unit 108 mechanically supports cannula 102 such that cannula 102 substantially establishes fluid communication with fluid reservoir 112 when the second housing 116 is engaged with first housing 110. Cannula 102 may include a first end 124 ("cannula first end 124"), a second end 126 ("cannula second end 126") opposite cannula first end 124, and a lumen 128 providing fluid communication cannula first end 124 and cannula second end 126. Cannula first end 124 may be configured to implant into body 101 of the use (e.g., using a first insertion needle (not shown)). Second unit 108 mechanically supports a portion of cannula 102 including cannula second end 126 such that cannula second end 126 inserts into a fluid access 130 of first unit 106 when second housing 116 engages first housing 110. Fluid access 130 is in fluid communication with fluid reservoir 112 (e.g., via first conduit 131). Thus, when cannula second end 126 inserts into fluid access 130, cannula 102 establishes fluid communication between fluid reservoir 112 and cannula first end 124. In examples, the portion of cannula 102 including cannula second end 126 is substantially affixed to second unit 108. That is, when second unit 108 is disengaged and displaced from first unit 106, cannula 102 may be configured to remain affixed to second unit 108, such that the separation of first unit 106 from second unit 108 causes cannula first end 124 to withdraw from body 101 of the user.

Infusion device 100 is configured to establish communication between sensor 104 of second unit 108 and processing circuitry 114 of first unit 106 when second housing 116 engages first housing 110. Some portion of sensor 104 may be configured to implant into body 101 of the use (e.g., using a second insertion needle (not shown)). In examples, first unit 106 includes first connector 132 in electrical communication with processing circuitry 114 (e.g., via communication link 134) and second unit 108 includes second connector 136 in electrical communication with sensor 104 (e.g., via communication link 138) to establish the communication between sensor 104 and processing circuitry 114. Infusion device 100 may be configured such that engagement of second housing 116 with first housing 110 causes second connector 136 to establish an electrical connection with first connector 132, such that sensor 104 may provide a signal to processing circuitry 114 indicative of a physiological characteristic of the user (e.g., a glucose level).

Second unit 108 may mechanically support second connector 136 and cannula 102 such that engagement of second housing 116 and first housing 110 causes cannula second end 126 to insert into fluid access 130 and second connector 136 to establish an electrical connection with first connector 132. Infusion device 100 may be configured such that, when fixation device 120 limits movement of second housing 116 relative to first housing 110, second cannula end 126 inserts into fluid access 130 and second connector 136 establishes the electrical connection with first connector 132. In examples, infusion device 100 is configured such that the engagement of second unit 108 with first unit 106 causes infusion device 100 to establish the fluid communication between fluid reservoir 112 and cannula first end 124 and/or the electrical connection between sensor 104 and processing circuitry 114. For example, second unit 108 may be caused to engage with first unit 110 by moving second unit 108 toward first unit 106 (e.g., in a distal direction D) until fixation device 120 acts to limit motion of second housing 116 relative to first housing 110. Fixation device 120 may act to limit motion of second housing 116 relative to first housing 110 in the distal direction D, a proximal direction P, or in any other direction.

Infusion device 100 may be configured to cause the implantation of cannula 102 and sensor 104 in the body 101 of the user when second unit 108 engages or is caused to engage with first unit 106. In examples, as will be discussed, second unit 108 includes a first insertion needle configured to cause the implantation of cannula first end 124 and a second insertion needle configured to cause the implantation of sensor 104 when second unit 108 engages or is caused to engage with first unit 106. The first insertion needle and second insertion needle may be configured to move substantially independently of first unit 106 and second unit 108 in the distal direction D, such that the first insertion needle and the second insertion needle may be withdrawn as second housing 116 remains engaged with first housing 100 (e.g., via fixation device 120) and cannula first end 124 and sensor 104 remain implanted within body 101 of the user.

First unit 106 and second unit 108 may have any shape, size, and/or configuration sufficient to allow second housing 116 to engage first unit 116 such that reservoir 112 is in fluid communication with cannula 102 and sensor 104 is in electrical communication with processing circuitry 114. In examples, first housing 110 defines a recess and some portion of second housing 116 may be configured to substantially insert into the recess when second housing 116 engages first housing 110, although this is not required. First housing 110 and second housing 116 may be configured in any manner such that movement of first housing 110 is limited relative to second housing 116 when second housing 116 engages first housing 110. First housing 110 and second housing 116 may have any shape, size, and/or configuration sufficient to support (e.g., mechanically support) the components of first unit 106 and second unit 108 respectively.

Figure 4A:
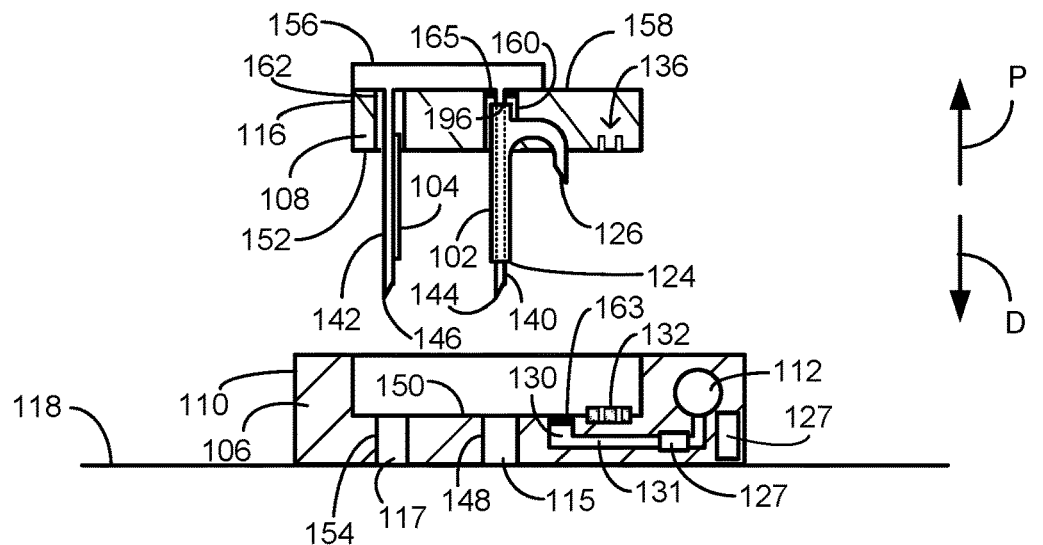
FIG. 4A is a schematic of a first unit and a second unit.
Figure 4B:
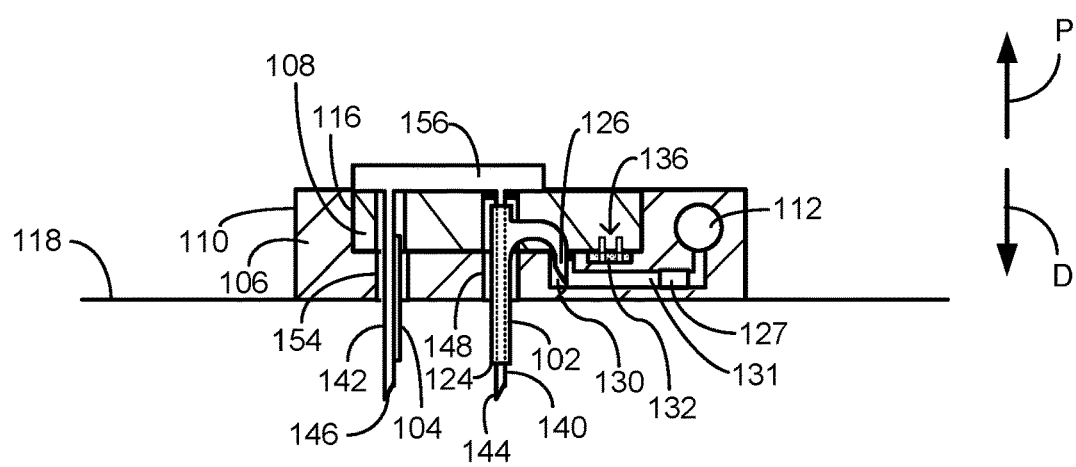
FIG. 4B is a schematic of the first unit and the second unit of FIG. 4A in another configuration.
Figure 4C:
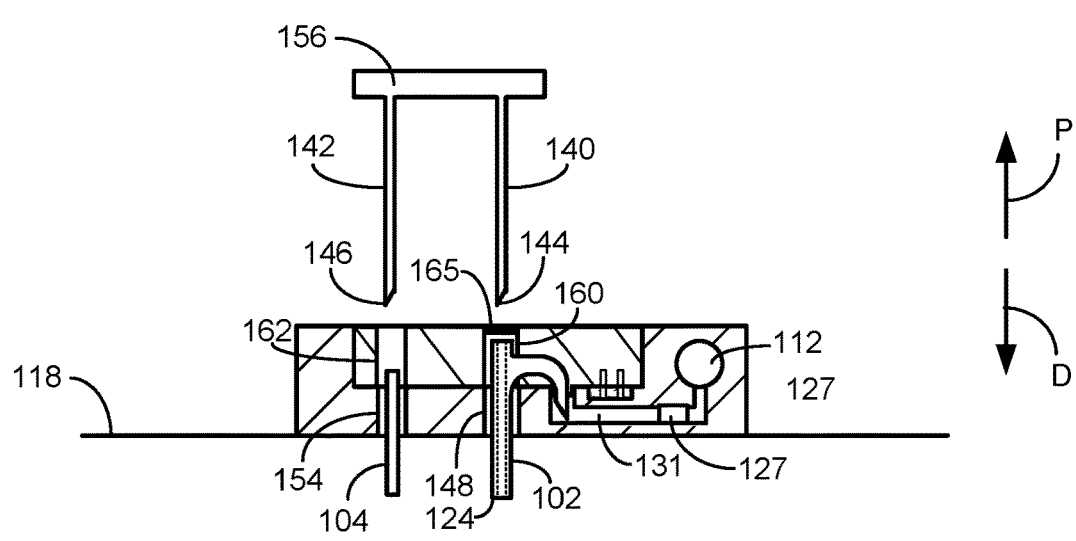
FIG. 4C is a schematic of the first unit and the second unit of FIG. 4A and FIG. 4B in a different configuration.

FIG. 4A illustrates infusion device 100 with first unit 106 positioned proximate the skin 118 of a user and second unit 108 in a disengaged position, such that second unit 108 is displaced from first unit 106. Second unit 108 includes first insertion needle 140 releasably engaged with cannula 102 and second insertion needle 142 releasably engaged with sensor 104. FIG. 4B illustrates infusion device 100 with second unit 108 having moved in the distal direction D to engage first unit 106. The engagement of second unit 108 with first unit 106 has caused first insertion needle 140 to implant cannula first end 124 and caused second insertion needle 142 to implant sensor 104 through skin 118 and into the user. FIG. 4C illustrates infusion device 100 with first insertion needle 140 and second insertion needle 142 withdrawn in the proximal direction P as second unit 108 remains engaged with first unit 106 and cannula first end 124 and sensor 104 remain implanted within the user.

First insertion needle 140 defines a distal end 144 ("first needle distal end 144") and second insertion needle 142 defines a distal end 146 ("second needle distal end 146") configured to pierce the skin 118 of the user. Infusion device 100 is configured such that, as discussed, first unit 106 may be proximate (e.g., in contact with) the skin 118 of the user when second unit 108 is displaced and substantially separated from first unit 106 (as depicted in FIG. 4A). Infusion unit 100 may be configured such that, when second unit 108 is moved in the distal direction D and engaged with first unit 106 (as depicted in FIG. 4B), the movement of second unit 108 toward first unit 106 causes first insertion needle 140 and second insertion needle 142 to extend through first unit 106 and pierce the skin 118 of the user, causing implantation of cannula 102 (e.g., cannula first end 124) and sensor 104. When first unit 106 is engaged with second unit 108, second unit 108 causes cannula second end 126 to insert into fluid access 130, such that fluid reservoir 112 is in fluid communication with cannula first end 124 (e.g., via first conduit 131), and causes second connector 136 to electrically connect with first connector 132, such that processing circuitry 114 is electrically connected to sensor 104. Infusion device 100 may be configured such that first insertion needle 140 and second insertion needle 142 may be proximally withdrawn and separated from first unit 106 and second unit 108 as cannula 102 and sensor 104 remain implanted in the user and second unit 108 remains engaged with first unit 106 (as depicted in FIG. 4C). Infusion device 100 remains configured to provide a fluid (e.g., insulin) to the user using cannula 102 and monitor a physiological characteristic (e.g., a glucose level) of the user using sensor 104 when first insertion needle 140 and second insertion needle 142 are withdrawn and separated from first unit 106 and second unit 108.

First unit 106 is configured such that first insertion needle 140 is translatable (e.g., in the distal direction D and/or proximal direction P) relative to first unit 106. In examples, first unit 106 defines a first channel 148 ("first unit first channel 148") extending through first housing 110. In examples, first unit 106 includes a facing surface 150 ("first facing surface 150") configured to substantially face second unit 108, and first unit first channel 148 defines a passage through first housing 110 from first facing surface 150 to first hole 115. In examples, second unit 108 defines a facing surface 152 ("second facing surface 152"), and first facing surface 150 is configured to substantially face second facing surface 152.

First unit first channel 148 is configured to accommodate passage of first insertion needle 140 and a portion of cannula 102 when second unit 108 is displaced in the distal direction D towards first unit 106 (e.g., when second facing surface 152 is moved toward first facing surface 150). In some examples, first insertion needle 140 and the portion of cannula 102 are configured to extend from second unit 108 and through first unit first channel 148 when second unit 108 is displaced in the distal direction D towards first unit 106. First insertion needle 140 and the portion of cannula 102 are configured to translate through first unit first channel 148 in the distal direction D relative to first unit 106, such that first insertion needle 140 and cannula 102 may extend through first unit first channel 148 to pierce the skin 118 of the user as second unit 108 is displaced in the distal direction D to engage second unit 108.

In examples, infusion device 100 includes a needle carrier 156 configured to cause first insertion needle 140 to translate through first unit first channel 148 in the distal direction D or in the proximal direction P. In examples, needle carrier 156 is configured to limit movement of first insertion needle 140 relative to needle carrier 156, such that movement of needle carrier 156 (e.g., in the distal direction D or proximal direction P) causes corresponding movement of first insertion needle 140 through first unit first channel 148. In examples, needle carrier 156 is configured to receive a force in the distal direction D and transmit at least some portion of the force in the distal direction D to first insertion needle 140 to cause, for example, first insertion needle 140 to move distally through first unit first channel 148. Needle carrier 156 may be configured to receive a force in the proximal direction P and transmit at least some portion of the force in the proximal direction P to first insertion needle 140 to cause, for example, first insertion needle 140 to move proximally through first unit first channel 148. Needle carrier 156 may be configured to cause the movement of first insertion needle 140 in any appropriate manner. In examples, first insertion needle 140 is substantially affixed to needle carrier 156 using a fastener, a clamp, an interference fit with needle carrier 156, or some other appropriate arrangement sufficient to allow needle carrier 156 to transmit a force to first insertion needle 140.

First insertion needle 140 may translate relative to first housing 110 and/or the second housing 116 in a first needle distal direction and/or in a first needle proximal direction. In examples, the first needle distal direction is a direction which would cause first needle distal end 144 to move away from first housing 110 while some portion of first insertion needle 140 is within first unit first channel 148. The first needle proximal direction is a direction which would cause first needle distal end 144 to move toward first housing 110 while some portion of first insertion needle 140 is within first unit first channel 148. First insertion needle 140 may translate in the first needle distal direction or the first needle proximal direction regardless of whether the portion of first insertion needle 140 is within first unit first channel 148, provided that the first needle distal direction and/or the first needle proximal direction would cause motion of the first needle distal end 144 as described if the portion of first insertion needle 144 were in first unit first channel 148.

First unit 106 is configured such that second insertion needle 142 is translatable (e.g., in the distal direction D and/or proximal direction P) relative to first unit 106. In examples, first unit 106 defines a second channel 154 ("first unit second channel 154") extending through first housing 110. In examples, first unit second channel 154 defines a passage through first housing 110 from first facing surface 150 to second hole 117.

First unit second channel 154 is configured to accommodate passage of second insertion needle 142 and at least a portion of sensor 104 when second unit 108 is displaced in the distal direction D towards first unit 106 (e.g., when second facing surface 152 is moved toward first facing surface 150). In some examples, second insertion needle 142 and sensor 104 are configured to extend from second unit 108 and through first unit second channel 154 when second unit 108 is displaced in the distal direction D towards first unit 106. Second insertion needle 142 and sensor 104 are configured to translate through first unit second channel 154 in the distal direction D relative to first unit 106, such that second insertion needle 142 and sensor 104 may extend through first unit second channel 106 to pierce the skin 118 of the user as second unit 108 is displaced in the distal direction D to engage second unit 108.

In examples, needle carrier 156 is configured to cause second insertion needle 142 to translate through first unit second channel 154 in the distal direction D or in the proximal direction P. In examples, needle carrier 156 is configured to limit movement of second insertion needle 142 relative to needle carrier 156, such that movement of needle carrier 156 (e.g., in the distal direction D or proximal direction P) causes corresponding movement of second insertion needle 142 through first unit second channel 154. In examples, needle carrier 156 is configured to receive a force in the distal direction D and transmit at least some portion of the force in the distal direction D to second insertion needle 142 to cause, for example, second insertion needle 142 to move distally through first unit second channel 154. Needle carrier 156 may be configured to receive a force in the proximal direction P and transmit at least some portion of the force in the proximal direction P to second insertion needle 142 to cause, for example, second insertion needle 142 to move proximally through first unit second channel 154. In examples, second insertion needle 142 is substantially affixed to needle carrier 156 using a fastener, a clamp, an interference fit with needle carrier 156, or some other appropriate arrangement sufficient to allow needle carrier 156 to transmit a force to second insertion needle 142.

Second insertion needle 142 may translate relative to first housing 110 and/or second housing 116 in a second needle distal direction and/or in a second needle proximal direction. In examples, the second needle distal direction is a direction which would cause second needle distal end 146 to move away from first housing 110 while some portion of second insertion needle 142 is within first unit second channel 154. The second needle proximal direction is a direction which would cause second needle distal end 146 to move toward first housing 110 while some portion of second insertion needle 142 is within first unit second channel 154. Second insertion needle 142 may translate in the second needle distal direction or the second needle proximal direction regardless of whether the portion of second insertion needle 142 is within first unit second channel 154, provided that the second needle distal direction and/or the second needle proximal direction would cause motion of second needle distal end 146 as described if the portion of second insertion needle 142 were in first unit second channel 154. The second needle distal direction may be similar to or substantially the same as the first needle distal direction. The second needle proximal direction may be similar to or substantially the same as the first needle proximal direction.

Infusion device 100 may be configured such that first insertion needle 140 and second insertion needle 142 pierce the skin 118 of the user substantially concurrently as second unit 108 moves in the distal direction D toward first unit 106 (e.g., as infusion device 100 transitions from the configuration of FIG. 4A to the configuration of FIG. 4B). Infusion device 100 may be configured such that first insertion needle 140 and second insertion needle 142 pierce the skin 118 substantially concurrently in order to, for example, limit discomfort to the user that might be caused by insertions separated by a user-discernable chronological time increment. In examples, needle carrier 156 is configured to cause substantially concurrent translation of first insertion needle 140 through first unit first channel 148 and second insertion needle 142 through first unit second channel 154. Needle carrier 156 may be configured to substantially concurrently translate first insertion needle 140 and second insertion needle 142 to cause first needle distal end 144 and second needle distal end 146 to pierce the skin 118 substantially concurrently.

In some examples, needle carrier 156 is configured to impart a force in the distal direction D to second unit 108 to cause second unit 108 to move distally toward first unit 106. In examples, needle carrier 156 is configured to receive a force in the distal direction D (e.g., from a inserter (not shown)) and transmit a portion of the force to second unit 108 to cause second unit 108 to move distally toward first unit 106. Infusion device 100 may be configured such that, when needle carrier 156 receives the force in the distal direction D, needle carrier 156 transmits a portion of the force to second housing 116, causing second unit 108 to contact first unit 106 (e.g., causing second facing surface 152 to contact first facing surface 150) and causing second housing 116 to engage first housing 110 (as depicted in FIG. 4B). In examples, needle carrier 156 is configured to impart the distal force on second unit 108 on a bearing surface 158 opposite the second facing surface 152 of second unit 108.

In examples, second unit 108 is configured such that first insertion needle 140 is translatable (e.g., in the distal direction D and/or proximal direction P) relative to second unit 108 to permit, for example, withdrawal of first insertion needle 140 from second unit 108 as second unit 108 remains engaged with first unit 106 (as depicted in FIG. 4C). In examples, second unit 108 defines a first channel 160 ("second unit first channel 160") extending through second housing 116. In examples, second unit first channel 160 defines a passage through second housing 116 between second facing surface 152 and a bearing surface 158. Second unit first channel 160 may be configured to accommodate passage of at least first insertion needle 140 when first insertion needle 140 is displaced in the proximal direction P away from second unit 108 (as depicted in FIG. 4C). In some examples, first insertion needle 140 and a portion of cannula 102 are configured to extend from second unit 108 through second unit first channel 160 when second unit 108 is displaced in the distal direction D towards first unit 106. First insertion needle 140 may be configured to translate through second unit first channel 160 in the proximal direction P relative to second unit 108, such that first insertion needle 140 may be withdrawn from second unit 108 following implantation of cannula 102.

Needle carrier 156 may be configured to cause first insertion needle 140 to translate through second unit first channel 160 in the proximal direction P when needle carrier 156 translates in the proximal direction P away from second unit 108. In examples, needle carrier 156 is configured to receive a force in the proximal direction P and transmit at least some portion of the force in the proximal direction P to first insertion needle 140 to cause, for example, first insertion needle 140 to move proximally through second unit first channel 160. In examples, needle carrier 156 is configured to receive a force in the proximal direction P (e.g., from a inserter (not shown)) and transmit a portion of the force to first insertion needle 140 to cause first insertion needle 140 to displace from second unit 108 in the proximal direction P.

In examples, second unit 108 is configured such that second insertion needle 142 is translatable (e.g., in the distal direction D and/or proximal direction P) relative to second unit 108 to permit, for example, withdrawal of second insertion needle 142 from second unit 108 as second unit 108 remains engaged with first unit 106 (as depicted in FIG. 4C). In examples, second unit 108 defines a second channel 162 ("second unit second channel 162") extending through second housing 116. In examples, second unit second channel 162 defines a passage through second housing 116 between second facing surface 152 and a bearing surface 158. Second unit second channel 162 may be configured to accommodate passage of at least second insertion needle 142 when second insertion needle 142 is displaced in the proximal direction P away from second unit 108 (as depicted in FIG. 4C). In some examples, second insertion needle 142 and a portion of sensor 104 are configured to extend from second unit 108 through second unit second channel 162 when second unit 108 is displaced in the distal direction D towards first unit 106. Second insertion needle 142 may be configured to translate through second unit second channel 162 in the proximal direction P relative to second unit 108, such that second insertion needle 142 may be withdrawn from second unit 108 following implantation of sensor 104.

Needle carrier 156 may be configured to cause second insertion needle 142 to translate through second unit second channel 162 in the proximal direction P when needle carrier 156 translates in the proximal direction P away from second unit 108. In examples, needle carrier 156 is configured to receive a force in the proximal direction P and transmit at least some portion of the force in the proximal direction P to second insertion needle 142 to cause, for example, second insertion needle 142 to move proximally through second unit second channel 162. In examples, needle carrier 156 is configured to receive a force in the proximal direction P (e.g., from a inserter (not shown)) and transmit a portion of the force to second insertion needle 142 to cause second insertion needle 142 to displace from second unit 108 in the proximal direction P.

Infusion device 100 may be configured such that first insertion needle 140 and second insertion needle 142 withdraw from the skin 118 of the user substantially concurrently needle carrier 156 moves in the proximal direction P away from second unit 108 (e.g., as infusion device 100 transitions from the configuration of FIG. 4B to the configuration of FIG. 4C). Infusion device 100 may be configured such that first insertion needle 140 and second insertion needle 142 withdraw from skin 118 substantially concurrently in order to, for example, limit discomfort to the user that might be caused by withdrawals separated by a user-discernable chronological time increment. In examples, needle carrier 156 is configured to cause substantially concurrent translation of first insertion needle 140 through second unit first channel 160 and second insertion needle 142 through second unit second channel 162. Needle carrier 156 may be configured to substantially concurrently translate first insertion needle 140 and second insertion needle 142 to cause first needle distal end 144 and second needle distal end 146 to withdraw from the skin 118 substantially concurrently.

In examples, infusion device 100 is configured to fluidly isolate fluid access 130 from portions of infusion device 100 in order to substantially prevent adverse impacts with may arise through contact with a fluid in fluid reservoir 112. The portions of infusion device may include, for example without limitation, first connector 132, second connector 136, first facing surface 150, second facing surface 152, and/or other components of first unit 106 and/or second unit 108. In examples, infusion device 100 includes an access septum 163 configured to fluidly isolate the portions of infusion device 100 and fluid access 130. Infusion device 100 may be configured such that, as second housing 116 engages first housing 110, cannula second end 126 punctures access septum 163 to place cannula second end 126 in fluid communication with fluid access 130. Access septum 163 may be comprised of a self-sealing material, such that access septum 163 substantially closes around cannula second end 126 to substantially maintain a fluid isolation between the portions of infusion device 100 and fluid access 130.

In examples, infusion device 100 is configured to fluidly isolate second unit first channel 160 from portions of infusion device 100 in order to substantially prevent adverse impacts with may arise through contact with a fluid flowing through cannula 102. The portions of infusion device may include, for example without limitation, first connector 132, second connector 136, first facing surface 150, second facing surface 152, and/or other components of first unit 106 and/or second unit 108. In examples, infusion device 100 includes a second septum 165 configured to fluidly isolate the portions of infusion device 100 and second unit first channel 160. Infusion device 100 may be configured such that first insertion needle 140 extends through second septum 165 when first insertion needle 140 extends through second unit first channel 160. Second septum 165 may be comprised of a self-sealing material, such that second septum 165 substantially closes around first insertion needle 140 to substantially maintain a fluid isolation between the portions of infusion device 100 and second unit first channel 160. Second septum 165 may be configured to self-seal when first insertion needle 140 is withdrawn through second septum 165 (e.g., withdrawn in the proximal direction P) to maintain the fluid isolation between the portions of infusion device 100 and second unit first channel 160 when first insertion needle 140 is displaced from second unit 108.

Figure 5:
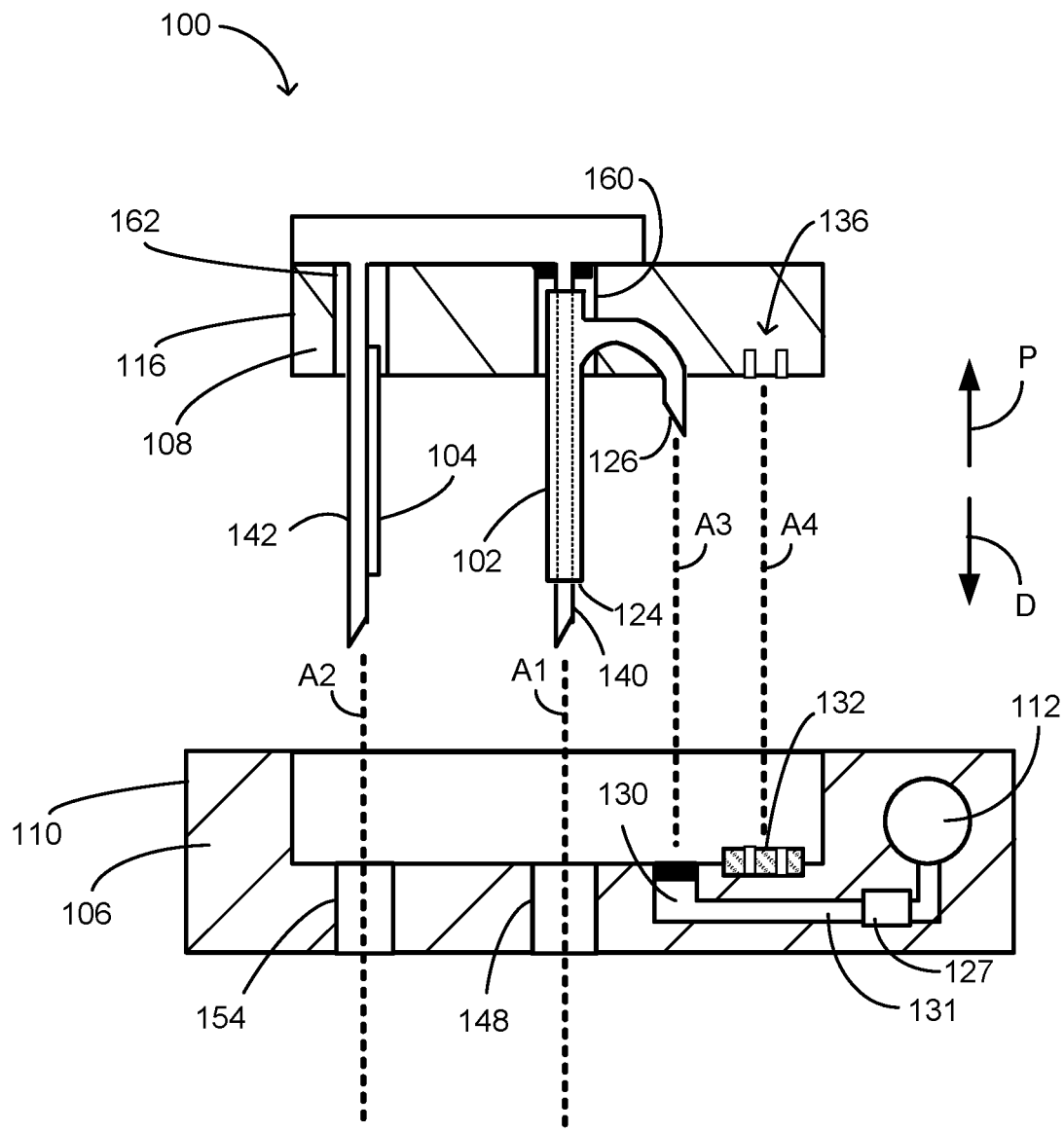
FIG. 5 is a schematic of second unit aligning with a first unit.

FIG. 5 illustrates an example infusion device configured to substantially align one or more components of first unit 106 and one or more components of second unit 108 such that infusion device configures to deliver a therapeutic fluid and monitor a physiological characteristic of a user when second unit 108 engages first unit 106. For example, second housing 116 may define an axis A1, and second unit 108 may be configured to translate first insertion needle 140 and a cannula first end 124 over the axis A1 when second unit 108 is translated toward first unit 106. In examples, second unit 108 is configured such that the axis A1 passes through first unit first channel 148 of first unit 106, such that movement of second unit 108 in the distal direction D toward first unit 106 causes first insertion needle 140 and cannula first end 124 to extend through first unit first channel 148. In examples, second housing 116 defines and axis A2 and is configured to translate second insertion needle 142 and a sensor 104 over the axis A2 when second unit 108 is translated toward first unit 106. Second unit 108 may be configured such that the axis A2 passes through first unit second channel 154 of first unit 106, such that movement of second unit 108 in the distal direction D toward first unit 106 causes second insertion needle 142 and sensor 104 to extend through first unit second channel 154.

In examples, second housing 116 defines the axis A1 and the axis A2 such that when the axis A1 passes through first unit first channel 148, the axis A2 passes through first unit second channel 154. Hence, second unit 108 may be configured to translate first insertion needle 140 and cannula first end 124 over axis A1 through first unit first channel 148 and translate second insertion needle 142 and sensor 104 over axis A2 through first unit second channel 154 when second unit 108 translates toward first unit 106 in the distal direction D. Second unit 108 may be configured to substantially align first insertion needle 140 and cannula first end 124 with first unit first channel 148 and substantially align second insertion needle 142 and sensor 104 with first unit second channel 154 when second unit 108 is in a disengaged position (e.g., displaced from first unit 106 (FIG. 4A, 5), such that engagement of second housing 116 with first housing 110 causes first insertion needle 140 and cannula first end 124 to pass through first unit first channel 148 and causes second insertion needle 142 and sensor 104 to pass through first unit second channel 154.

In examples, second housing 116 defines an axis A3. Second unit 108 may be configured to translate cannula second end 126 over the axis A3 when second unit 108 is translated toward first unit 106. In examples, second unit 108 is configured such that the axis A3 passes through fluid access 130 of first unit 106, such that movement of second unit 108 in the distal direction D toward first unit 106 causes cannula second end 126 to insert within fluid access 130 and establish fluid communication between fluid reservoir 112 and cannula first end 124 (e.g., via first conduit 131). Second housing 116 may define the axis A3 such that, when the axis A3 passes through fluid access 130, the axis A1 passes through first unit first channel 148 and/or the axis A2 passes through first unit second channel 154. Hence, second unit 108 may be configured to substantially align cannula second end 126 with fluid access 130, substantially align first insertion needle 140 and cannula first end 124 with first unit first channel 148, and/or substantially align second insertion needle 142 and sensor 104 with first unit second channel 154. Second unit 108 may be configured such that, when second unit 108 is in a disengaged position (e.g., displaced from first unit 106 (FIG. 4A, 5), engagement of second housing 116 with first housing 110 causes second cannula end 126 to insert into fluid access 130, causes first insertion needle 140 and cannula first end 124 to pass through first unit first channel 148, and/or causes second insertion needle 142 and sensor 104 to pass through first unit second channel 154.

In examples, second housing 116 defines an axis A4. Second unit 108 may be configured to translate second connector 136 over the axis A4 when second unit 108 is translated toward first unit 106. In examples, second unit 108 is configured such that the axis A4 passes through first connector 132 of first unit 106, such that movement of second unit 108 in the distal direction D toward first unit 106 causes second connector 136 to contact first connector 132 and establish electrical communication between sensor 104 and processing circuitry 114. Second housing 116 may define the axis A4 such that, when the axis A4 passes through first connector 132, the axis A1 passes through first unit first channel 148, the axis A2 passes through first unit second channel 154, and/or the axis A3 pass through fluid access 130. Hence, second unit 108 may be configured to substantially align second connector 136 with first connector 132, substantially align first insertion needle 140 and cannula first end 124 with first unit first channel 148, substantially align second insertion needle 142 and sensor 104 with first unit second channel 154, and/or substantially align cannula second end 126 with fluid access 130. Second unit 108 may be configured such that, when second unit 108 is in a disengaged position (e.g., displaced from first unit 106 (FIG. 4A, 5), engagement of second housing 116 with first housing 110 causes second connector 136 to contact first connector 132, causes first insertion needle 140 and cannula first end 124 to pass through first unit first channel 148, causes second insertion needle 142 and sensor 104 to pass through first unit second channel 154, and/or causes cannula second end 126 to insert into fluid access 130.

Figure 6A:
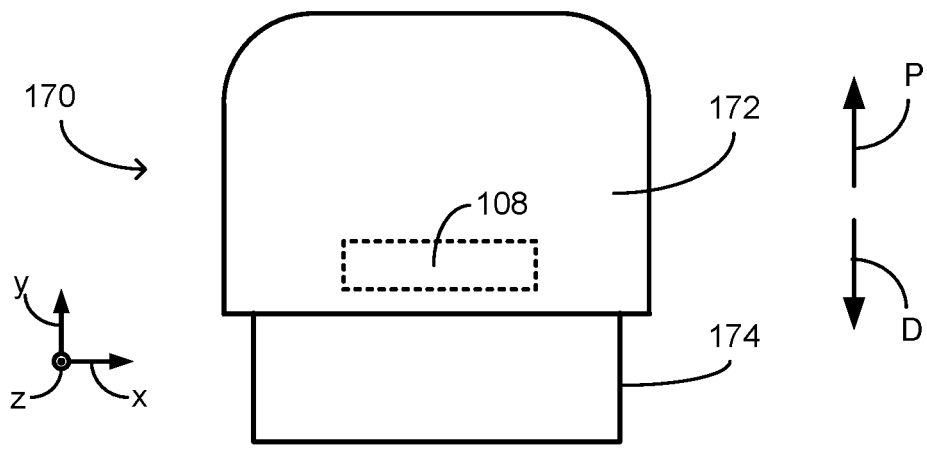
FIG. 6A is a first view of an inserter and a second unit.
Figure 6B:
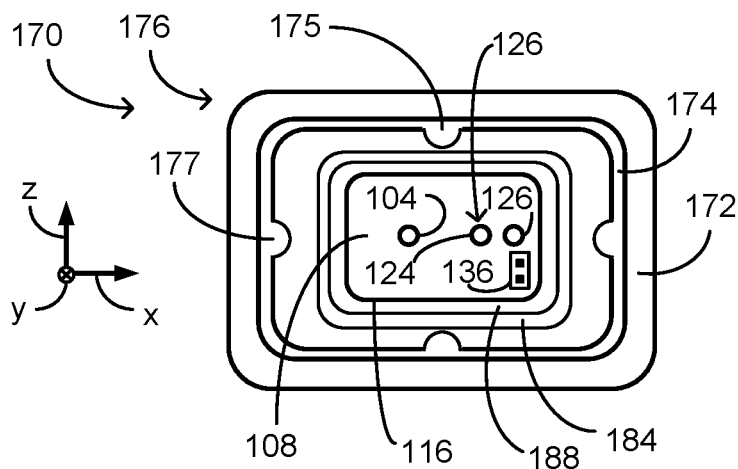
FIG. 6B is a second view of the inserter and second unit of FIG. 6A.

FIG. 6A and FIG. 6B illustrate an inserter 170 configured to cause second housing 116 of second unit 108 to engage first housing 110 of first unit 106. Inserter 170 is configured to hold second unit 108 is a disengaged position wherein second unit 108 is displaced from first unit 106 (e.g., FIG. 4A). Inserter 170 is configured to cause second unit 108 to move to an engaged position wherein second housing 116 engages first housing 110 (e.g., FIG. 4B), to cause implantation of cannula 102 and sensor 104 using first insertion needle 140 and second insertion needle 142 respectively. Inserter 170 may be configured to withdraw first insertion needle 140 and second insertion needle 142 (e.g., FIG. 4C) following the implantation of cannula 102 and sensor 104. FIG. 6A and FIG. 6B illustrate an example inserter 170 with reference to the x-y-z axes shown. The z axis proceeds out of the page in FIG. 6A and the y axis proceeds into the page in FIG. 6B. Inserter 170 is depicted holding second unit 108 in the disengaged position in FIG. 6A and FIG. 6B, with second unit 108 hidden and illustrated in dashed lines in FIG. 6A.

Inserter 170 may be configured to allow a user to cause inserter 170 to engage second housing 116 and first housing 110 to cause the implantation of cannula 102 and sensor 104. In examples, inserter 170 includes a plunger 172 configured for manipulation by the user to cause the implantation. Plunger 172 may be engaged with a serter member 174 configured align second unit 108 and first unit 106, such that when inserter 170 causes the engagement of second housing 116 and the first housing 110, the components of first unit 106 and second unit 108 cooperatively operate to provide a therapeutic fluid (e.g., insulin) to the user using cannula 102 and monitor a physiological characteristic of the user (e.g., a glucose level) using sensor 104. In examples, inserter 170 is configured such that a user may cause plunger 172 to translate in the distal direction D relative to serter member 174 to commence the implantation of cannula 102 and sensor 104.

Inserter 170 may be configured to mate with first unit 106 when inserter 170 holds second unit 108 in the disengaged position. In examples, inserter 170 (e.g., serter member 174) includes one or more alignment members 176 including member 175 and member 177 configured to mate with first unit 106. Alignment members 176 may be configured such that, when inserter 170 mates with first unit 106, inserter 170 causes axis A1 (FIG. 5) to pass through first insertion needle 140 and first unit first channel 148, axis A2 to pass through second insertion needle 142 and first unit second channel 154, axis A3 to pass through cannula second end 126 and fluid access 130, and/or axis A4 to pass through second connector 136 and first connector 132.

Figure 7:
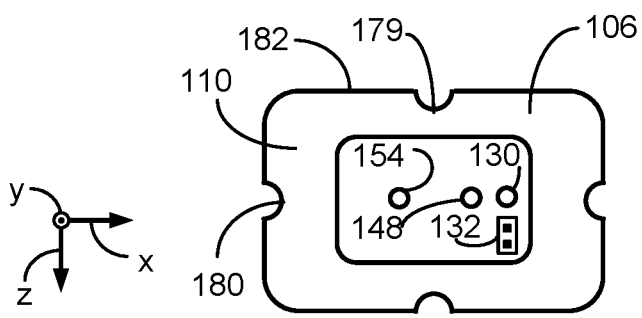
FIG. 7 is a schematic of a second unit.

FIG. 7 illustrates an example first unit 106 including first housing 110, first unit first channel 148, first unit second channel 154, fluid access 130, and first connector 132. The x-y-z axis of FIGS. 6A, 6B is included for reference, with the y axis proceeding out of the page. In examples, first housing 110 defines one or more aligning members 178, including member 179 and member 180. In examples, first housing 110 defines aligning members 178 around an outer perimeter 182 of first housing 110. In examples, insertor 170 is configured to mate with first unit 106 by causing alignment members 176 of insertor 170 to engage aligning members 178 of first unit 106. For example, one or more of alignment members 176 may define a protrusion configured to insert into a recess defined by one or more of aligning members 178. In examples, one or more of alignment members 176 may define a recess configured to insert into a protrusion of one or more of aligning members 178.

Insertor 170 may be configured to translate relative to first unit 106 (e.g., in the distal direction D) to cause the engagement between alignment members 176 and aligning members 178. For example, insertor 170 may be configured to be translated in the distal direction D such that insertor 170 (e.g., serter member 174) substantially surrounds outer perimeter 182 of first unit 106 when alignment members 176 engage aligning members 178. Insertor 170 may be configured such that, when alignment members 176 engage aligning members 178, insertor 170 causes axis A1 (FIG. 5) to pass through first insertion needle 140 and first unit first channel 148, axis A2 to pass through second insertion needle 142 and first unit second channel 154, axis A3 to pass through cannula second end 126 and fluid access 130, and/or axis A4 to pass through second connector 136 and first connector 132. Hence, insertor 170 may be configured to substantially align second unit 108 and first unit 106 such that when inserter 170 causes the engagement of second housing 116 and the first housing 110, the components of first unit 106 and second unit 108 cooperatively operate to provide a therapeutic fluid (e.g., insulin) to the user using cannula 102 and monitor a physiological characteristic of the user (e.g., a glucose level) using sensor 104.

Figure 8A:
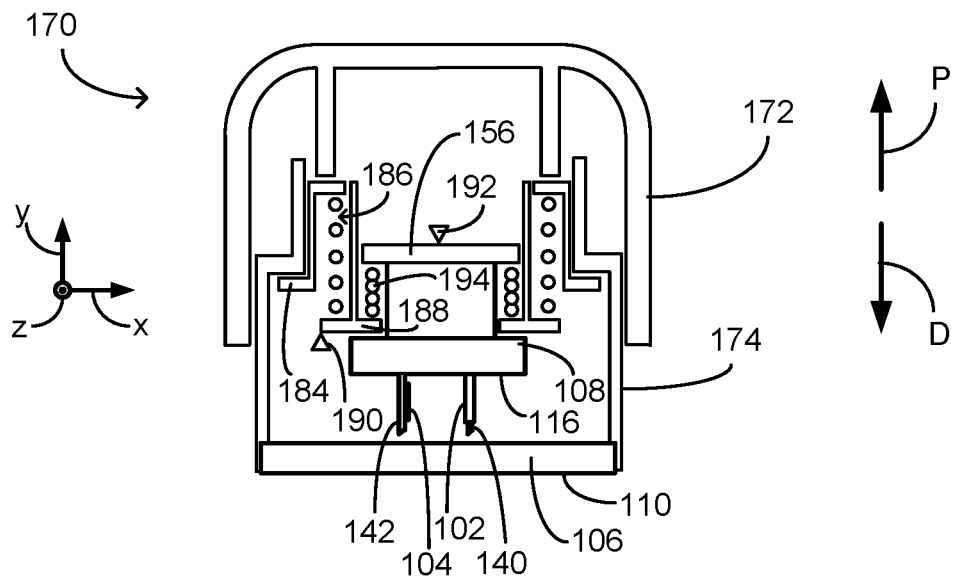
FIG. 8A is a schematic of an inserter in a first configuration.

FIG. 8A illustrates a cross-section of insertor 170 with a cutting plane taking parallel to the page. The x-y-z axes of FIGS. 6A, 6B, and 7 are included for reference, with the z axis proceeding out of the page. Insertor 170 includes serter member 174 and is holding second unit 108 in the disengaged position relative to first unit 106. Serter member 174 is engaged with first unit 106 such that axis A1 (FIG. 5) passes through first insertion needle 140 and first unit first channel 148, axis A2 passes through second insertion needle 142 and first unit second channel 154, axis A3 passes through cannula second end 126 and fluid access 130, and axis A4 to passes through second connector 136 and first connector 132.

Insertor 170 includes a charging member 184 configured to compress an insertion spring 186. Charging member 184 may be configured to compress insertion spring 186 when plunger 172 imparts a force (e.g., in the distal direction D) on charging member 184. In examples, charging member 184 is configured to translate relative to serter member 174 when plunger 172 translates relative to serter member 174 to cause the compression of insertion spring 186. Charging member 184 may be configured to exert a force (e.g., in the distal direction D) on insertion spring 186 to cause the compression of insertion spring 186.

In examples, insertor 170 includes a discharging member 188 configured to exert a force on insertion spring 186 opposite the force exerted by charging member 184 when charging member 184 compresses insertion spring 186. In examples, insertion spring 186 is configured to compress substantially between charging member 184 and discharging member 188. Discharging member 188 may be configured to remain substantially stationary with respect to serter member 174 when charging member 184 translates relative to serter member 174 (e.g., under the influence of plunger 172), such that the relative motion between charging member 184 and discharging member 188 causes the compression of insertion spring 186. In some examples, inserter 170 includes a release device 190 configured to maintain discharging member 188 substantially stationary relative to serter member 174 as charging member 184 translates relative to serter member 174.

Figure 8B:
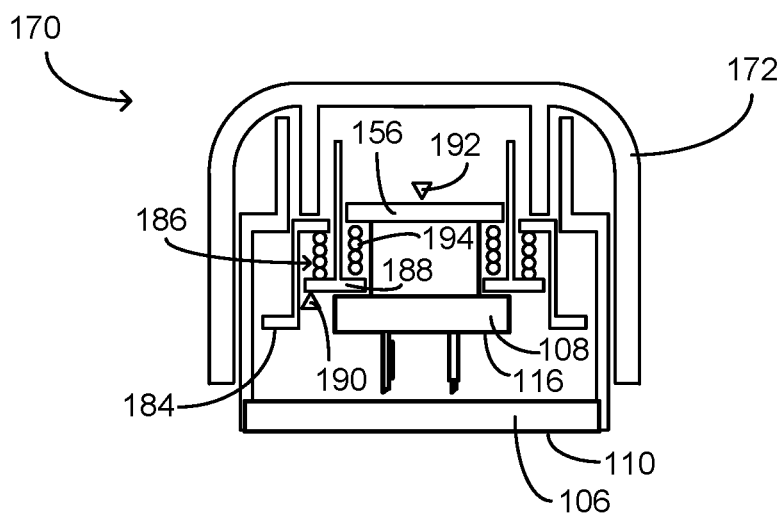
FIG. 8B is a schematic of the inserter of FIG. 8A in a second configuration.

As an example, FIG. 8B illustrates insertor 170 with plunger 172 having translated distally relative to serter member 174 to cause the compression of insertion spring 186. Having compressed insertion spring. The translation of plunger 172 has caused charging member 184 to translate relative to serter member 174. Insertion spring 186 has been compressed as charging member 184 translated relative to serter member 174 as discharging member 184 remained substantially stationary relative to serter member 174 (e.g., due to release device 190). In examples, and as depicted at FIGS. 8A and 8B, first unit 106 may be configured to remain substantially stationary with respect to discharging member 188 when charging member 184 translates relative to discharging member 188.

Discharging member 188 may be configured to exert a force on second unit 108 to cause movement of second unit 108 relative to first unit 106, and relative to serter member 174. In examples, insertion spring 186 is configured to exert a spring force on discharging member 188 to cause the movement. Insertor 170 may be configured such that, when charging member 184 translates relative to serter member 174 by a certain amount (causing charging of insertion spring 186), insertor 170 causes release device 190 to disengage from discharging member 188, such that insertion spring 186 may cause movement of discharging member 188 relative to serter member 174. The movement of discharging member 188 relative to serter member 174 may cause discharging member 188 to exert a force on second unit 108 (e.g., in the distal direction D), causing second unit 108 to move towards first unit 106.

Figure 8C:
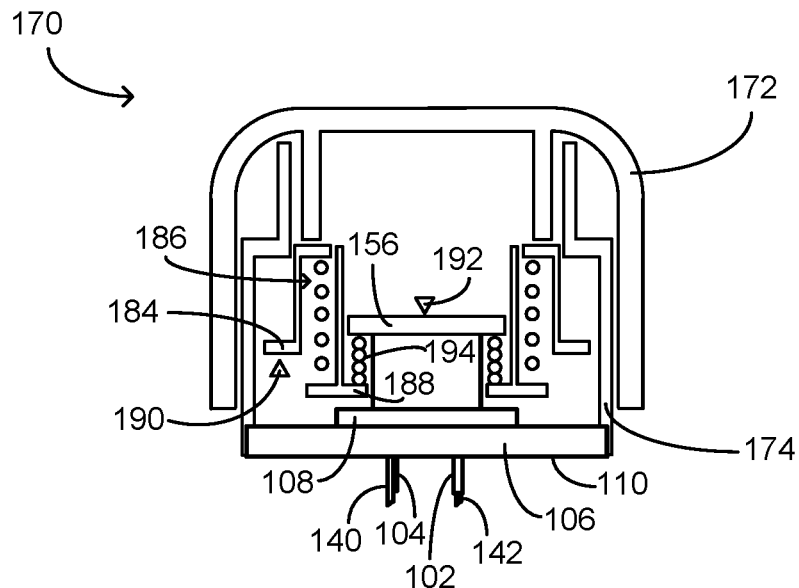
FIG. 8C is a schematic of the inserter of FIG. 8A and FIG. 8B in a third configuration.

FIG. 8C illustrates insertor 170 having caused release device 190 to disengage from discharging member 188. Insertion spring 186 has exerted a force (e.g., in the distal direction D) on discharging member 188, causing movement of discharging member 188 (e.g., in the distal direction D). The movement of discharging member 188 has caused discharging member 188 to exert a force on second unit 108, causing movement of second unit 108 (e.g., in the distal direction D) toward first unit 106.

In FIG. 8C, the movement of second unit 108 toward first unit 106 has caused second housing 116 to engage first housing 110, such that first housing 110 substantially limits movement of second housing 116 relative to first housing 110. For example, movement of second unit 108 toward first unit 106 may cause fixation device 120 (FIGS. 1, 3) to substantially secure second housing 116 in a position relative to first housing 110. Further, the movement of second unit 108 toward first unit 106 has extended first insertion needle 140 and cannula first end 124 through first unit first channel 148 (FIGS. 4A-4C) and second insertion needle 142 and sensor 104 through first unit second channel 154 (FIGS. 4A-4C). The extension of first insertion needle 140 and second insertion needle 142 causes implantation of cannula first end 124 and sensor 104 into the user.

Further, in FIG. 8C, the movement of second unit 108 toward first unit 106 has caused cannula second end 126 (FIG. 6B) to insert within fluid access 130 (FIG. 7) to establish fluid communication between fluid reservoir 112 (FIGS. 3, 4A-4C) and cannula first end 124 (FIG. 6B). The movement of second unit 108 toward first unit 106 has caused second connector 136 (FIG. 6B) to electrically connect with first connector 132 (FIG. 7) to establish electrical connection between processing circuitry 114 (FIGS. 3, 4A-4C) and sensor 104.

In examples, and as depicted at FIG. 8C, needle carrier 156 may be configured to remain substantially stationary with to second unit 108 when discharging member 188 causes movement of second unit 108. In examples, inserter 170 includes a release device 192 configured to maintain needle carrier 156 substantially stationary relative to second unit 108 when discharging member 188 causes second unit 108 to move toward first unit 106.

In examples, insertor 170 includes a withdrawal spring 194 configured to cause first insertion needle 140 and second insertion needle 142 to move relative to second unit 108 (and first unit 106 when second housing 116 is engaged with first housing 110). In examples, withdrawal spring is configured to cause a force (e.g., in the proximal direction P) to impart on first insertion needle 140 and second insertion needle 142 to cause the movement. Insertor 170 may be configured to cause first insertion needle 140 to move relative to second unit 108 through second unit first channel 160 (FIGS. 4A-4C). Insertor 170 may be configured to cause second insertion needle 142 to move relative to second unit 108 through second unit second channel 162 (FIGS. 4A-4C). In some examples, withdrawal spring 194 is configured to exert a force on needle carrier 156 to cause movement of needle carrier 156 relative to second unit 108, and needle carrier 156 is configured to transmit at least some portion of the force to first insertion needle 140 and second insertion needle 142 to cause the movement of first insertion needle 140 and second insertion needle 142 relative to second unit 108.

Figure 8D:
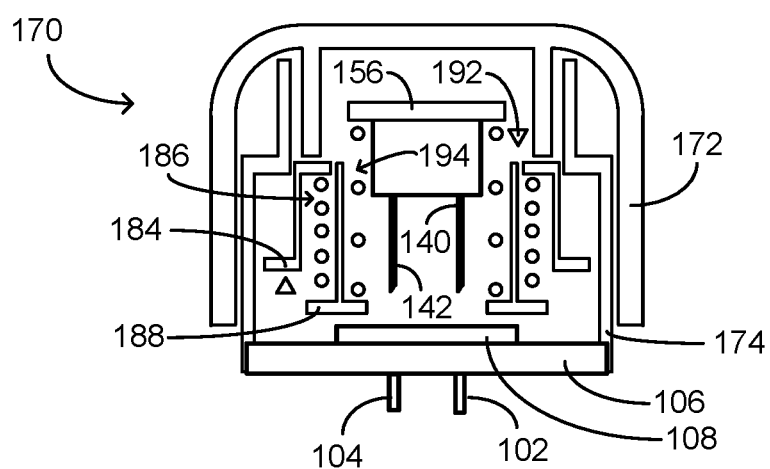
FIG. 8D is a schematic of the inserter of FIG. 8A, FIG. 8B, and FIG. 8C in a fourth configuration.

FIG. 8D illustrates insertor 170 having caused release device 192 to disengage from needle carrier 156, such that first insertion needle 140 and second insertion needle 142 may move proximally relative to second unit 108. Withdrawal spring 194 has discharged to cause a force (e.g., in the proximal direction P) to impart on first insertion needle 140 and second insertion needle 142 to cause the movement. In examples, withdrawal spring 194 exerts a force in the proximal direction P on needle carrier 156 causing movement of needle carrier 156 in the proximal direction, and the movement of needle carrier 156 cause movement of first insertion needle 140 and second insertion needle 142 relative to second unit 108.

Release device 190 may have any configuration sufficient engage to maintain discharging member 188 substantially stationary relative to serter member 174 as charging member 184 translates relative to serter member 174, and sufficient to disengage to allow insertion spring 186 to cause movement of discharging member 188 relative to serter member 174. Release device 192 may have any configuration sufficient to engage to maintain needle carrier 156 substantially stationary relative to second unit 108 when discharging member 188 causes second unit 108 to move toward first unit 106, and sufficient to disengage to allow first insertion needle 140 and second insertion needle 142 to translate proximally relative to second unit 108. Release device 190, 192 may include, for example, a mechanical switch configured to be actuated by some portion of or structure of inserter 170, a magnetic switch configured to actuate based on a position of some portion of or structure of inserter 170, an actuated device configured to be actuated by a position sensor included in inserter 170, a specific structure of inserter 170, and/or a device configured to actuate using other arrangements.

As discussed, first insertion needle 140 is configured to implant cannula first end 124 within a user, and configured to release cannula first end 124 when first insertion needle 140 is withdrawn, such that first insertion needle 140 may displace from second unit 108 as cannula first end 124 remains implanted in the user. Second insertion needle 142 is configured to implant sensor 104 within a user, and configured to release sensor 104 when second insertion needle 142 is withdrawn, such that second insertion needle 142 may displace from second unit 108 as sensor 104 remains implanted in the user.

In examples, first insertion needle 140 is configured to engage cannula 102 to cause cannula first end 124 to translate in the first direction toward the user (e.g., the distal direction D) when first insertion needle 140 translates in the first direction. First insertion needle 140 may be configured to exert a force on cannula 102 in the first direction to cause the translation of cannula first end 124. In examples, first insertion needle 140 and/or cannula 102 includes a first structural feature configured to cause first insertion needle 140 to exert the force in the first direction on cannula 102. First insertion needle 140 may be configured to disengage from (e.g., release) cannula 102 when first insertion needle 140 is subsequently withdrawn in the second direction opposite the first direction (e.g., in the proximal direction P). For example, first insertion needle 140 and/or cannula 102 may include a structural feature (the same as the first structural feature or a different structural feature) configured to allow first insertion needle 140 to move substantially independently of cannula 102 when first insertion needle 140 retracts in the second direction.

First insertion needle 140 may be configured to engage cannula 102 in any manner sufficient to cause first insertion needle 140 to translate cannula first end 124 in the first direction toward the user, and/or to allow first insertion needle 140 to move substantially independently of cannula 102 as first insertion needle 140 retracts in the second direction. In some examples, first insertion needle 140 is configured to at least partially extend within lumen 128 to cause the translation of cannula first end 124 in the first direction (e.g., the distal direction D). First insertion needle 140 may be configured to extend within lumen 128 when first insertion needle 140 moves substantially independently of cannula 102 as first insertion needle 140 retracts in the second direction. In other examples, first insertion needle 140 may be configured to substantially surround some portion of cannula 102 to cause the translation of cannula first end 124 in the first direction and/or allow first insertion needle 140 to move substantially independently of cannula 102 as first insertion needle 140 retracts in the second direction.

In some examples, cannula 102 defines a T-junction wherein cannula first end 124 defines an opening at one end of the cross bar of the T-junction and cannula 102 defines a needle access 196 (FIG. 4A) at the other end of the cross bar. In examples, first insertion needle 140 is configured to extend through lumen 128 of cannula 102 by extending through needle access 196 and cannula first end 124. First insertion needle 140 may be configured to withdraw through needle access 196 when infusion device 100 causes first insertion needle 140 to retract as cannula first end 124 remains implanted in the user. In examples, second septum 165 is configured to fluidly isolate needle access 196 and portions of infusion device 100 such as first connector 132, second connector 136, first facing surface 150, second facing surface 152, and/or other components of first unit 106 and/or second unit 108. Second septum 165 may be configured to self-seal when first insertion needle 140 withdraws (e.g., in the distal direction D) through second septum 165 to substantially maintain the fluid isolation.

In examples, first insertion needle 140 is configured to substantially mate with cannula 102 when first insertion needle 140 exerts the force in the first direction (e.g., the distal direction D) on cannula 102. First insertion needle 140 may be configured such that a subsequent force in the second direction (e.g., the proximal direction P) causes first insertion needle 140 to unmate (e.g., disengage) and move independently of cannula 102. In examples, first insertion needle 140 includes a bearing surface configured such that, when the force in the first direction is exerted on first insertion needle 140, the bearing surface engages a portion of cannula 102 and transmits some portion of the force to cannula 102, and when a force in the second direction is exerted on first insertion needle 140, the bearing surface displaces from cannula 102, such that first insertion needle 140 moves independently of cannula 102. Hence, infusion device 100 may be configured to withdraw first insertion needle 140 independently from cannula 102, such that cannula first end 124 remains implanted as first insertion needle 140 retracts.

As discussed, second insertion needle 142 is configured to releasably engage sensor 104 to cause the implantation of sensor 104 within the user. Second insertion needle 142 and sensor 104 may be cooperatively configured and arranged such that the second insertion needle 142 releasably carries at least a portion (e.g., a distal portion) of sensor 104 as second insertion needle 142 extends in the first direction toward the user (e.g., in the distal direction D). Second insertion needle 142 may be configured to engage sensor 104 in any manner sufficient to cause second insertion needle 142 to translate sensor 104 in the first direction toward the user, and/or to allow second insertion needle 142 to move substantially independently of sensor 104 as second insertion needle 142 retracts in the second direction.

In some examples, second insertion needle 142 configured to at least partially surround sensor 104 to carry sensor 104 as second insertion needle 142 extends through first unit 110 in the first direction. Second insertion needle 142 may be configured as a substantially hollow needle defining a void that accommodates sensor 104 within the void. Second insertion needle 142 and/or the sensor 104 may be configured such that second insertion needle 142 mechanically engages the sensor 104 when second insertion needle 142 extends in the first direction (e.g., the distal direction D) and disengages from sensor 104 when second insertion needle 142 retracts in the second direction (e.g., in the proximal direction P). In other examples, second insertion needle 142 may be configured to substantially insert into some portion of sensor 104 (e.g., such that some portion of sensor 104 substantially surrounds some portion of second insertion needle 142) to cause the translation of sensor 104 in the first direction, and/or to allow second insertion needle 142 to move substantially independently of sensor 104 as second insertion needle 142 retracts in the second direction.

In examples, second insertion needle 142 and/or sensor 104 include a second structural feature (e.g., the void defined by second insertion needle) configured to cause second insertion needle 142 to exert a force on sensor 104 when second insertion needle 142 extends in the first direction. Second insertion needle 142 may be configured to engage sensor 104 to cause implantation of sensor 104 in the user as second insertion needle 142 extends in the first direction. Sensor 104 may be configured to extend from first housing 110 when second insertion needle 142 causes the implantation of sensor 104 within the user.

Second insertion needle 142 may be configured to disengage from (e.g., release) sensor 104 when second insertion needle 142 is subsequently retracted in the second direction (e.g., in the proximal direction P). For example, second insertion needle 142 and/or sensor 104 may include a structural feature (the same as the second structural feature or a different structural feature) configured to allow second insertion needle 142 to move substantially independently of sensor 104 when second insertion needle 142 retracts in the second direction. In some examples, second insertion needle 142 is configured such that body tissue within the user engages with sensor 104 when second insertion needle 142 retracts, such that sensor 104 remains implanted in the user when second insertion needle 142 is withdrawn from the user. For example, second insertion needle 142 may include a portion (e.g., a distal portion) defining a longitudinal opening, such that a portion of sensor 104 is exposed to body tissue when second insertion needle 142 is inserted in the user. The body tissue may act to grip (e.g., frictionally engage) the exposed portion of sensor 104 as second insertion needle 142 is retracted, such that second insertion needle 142 may be withdrawn as sensor 104 remains implanted in the user. In examples, sensor 104 may include one or more structural features configured to assist the frictional engagement with the body tissue. In some examples, infusion device 100 may be configured to mechanically engage sensor 104 to hold sensor 104 in place (e.g., within the user) when second insertion needle 142 is retracted in the second direction.

Sensor 104 may be fabricated using a flexible or pliable substrate or carrier. In examples, sensor 104 is initially provided in a folded, serpentine, coiled, or accordion shape to, for example, provide a desired amount of slack to accommodate extension sensor 104 while sensor 104 is electrically coupled to second connector 136. Sensor 104 may be configured such that, as second insertion needle 142 carries sensor 104 in the second direction (e.g., in the distal direction D), sensor 104 extends without losing electrical contact with second connector 136.

First connector 132 and/or second connector 136 may have any configuration sufficient to allows first connector 132 and second connector 136 to establish electrical communication when second housing 116 engages first housing 110. In examples, first connector 132 and/or second connector 136 includes a flexible or pliable block substantially encasing and/or supporting one or more conductors. In examples, the block comprises silicone and/or some other substantially insulative material. In examples, the conductors comprise carbon pillars and/or some other substantially conductive material. In some examples, first connector 132 and/or second connector 136 is configured to compress (e.g., decrease volume) when second housing 116 engages first housing 110 and first connector 132 and second connector 136 establish electrical communication.

Figure 9:
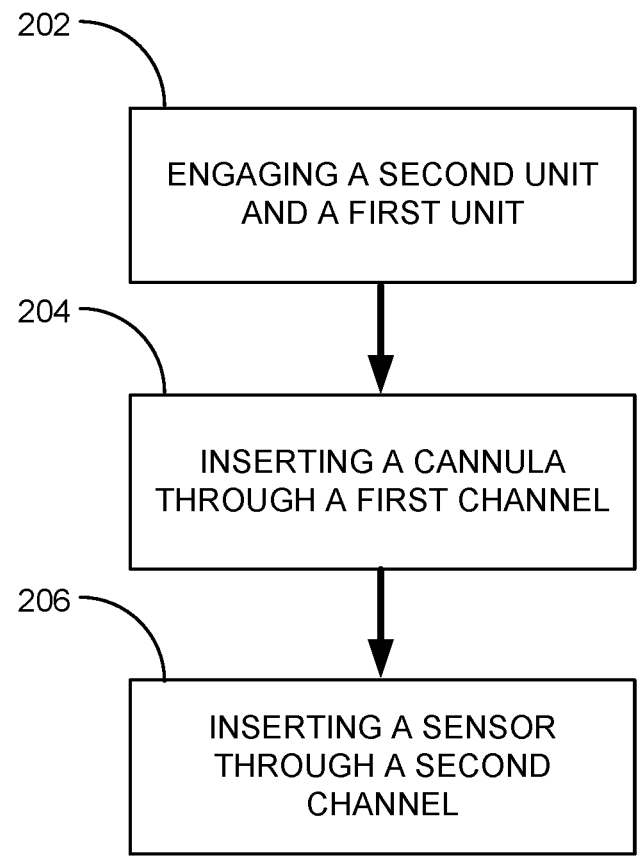
FIG. 9 illustrates an example technique of using an infusion device.

A technique for implanting a cannula and a sensor within a user is illustrated in FIG. 9. Although the technique is described mainly with reference to infusion device 100 of FIG. 1 through FIG. 8D, the technique may be applied to other infusion devices in other examples.

The technique includes engaging a second housing 116 of a second unit 108 with a first housing 110 of a first unit 106 (202). The first housing 110 may be proximate the skin 118 of the user. The first unit 106 may include a fluid reservoir 112 and processing circuitry 114. The second unit 108 may include a first insertion needle 140 and a second insertion needle 142. The technique may include releasably engaging cannula 102 using first insertion needle 140 and releasably engaging sensor 104 using second insertion needle 142.

The technique includes inserting cannula 102 through a first unit first channel 148 (204) and inserting sensor 104 through a first unit second channel (206). First unit first channel 148 and first unit second channel 154 may be defined by first housing 110. In examples, the technique includes inserting cannula 102 through first unit first channel 148 using first insertion needle 140. The technique may include inserting sensor 104 through first unit second channel 154 using second insertion needle 142. In examples, the technique includes causing first insertion needle 140 to extend through first unit first channel 148 by translating second unit 108 towards (e.g., in a distal direction D) first unit 110. The technique may include causing second insertion needle 142 to extend through first unit second channel 154 by translating second unit 108 towards (e.g., in the distal direction D) first unit 110.

The technique may include extending first insertion needle 140 through first unit first channel 148 and through a first hole 115 defined by first housing 110. The technique may include translating cannula first end 124 through first hole 115. First hole 115 may be defined in a base surface 111 of first housing 110 configured to position proximate the skin 118 of the user. The technique may include piercing the skin 118 of the user with a first needle distal end 144 and causing cannula first end 124 to implant within the user. In examples, the technique includes extending second insertion needle 142 through first unit second channel 154 and through a second hole 117 defined by first housing 110. The technique may include translating at least a portion of sensor 104 through second hole 117 (206). Second hole 117 may be defined in base surface 111 of first housing 110. The technique may include piercing the skin 118 of the user with a second needle distal end 146 and causing at least the portion of sensor 104 to implant within the user.

The technique may include causing second housing 116 to engage first housing 110 such that first housing 110 substantially limits motions of second housing 116 relative to first housing 110. In examples, the technique includes causing second housing 116 to limit relative motion of second housing 116 using a fixation device 120.

In examples, the technique includes inserting cannula second end 126 into a fluid access 130 when second housing 116 engages first housing 110. Fluid access 130 may be defined by first housing 110. In examples, fluid access 130 is in fluid communication with fluid reservoir 112 of first unit 110. In examples, the technique includes establishing fluid communication with cannula 102 and fluid reservoir 112 when cannula second end 126 inserts into fluid access 130. In examples, the technique includes establishing fluid communication between fluid reservoir 112 and cannula first end 124 via a lumen 128 of cannula 102. The technique may include causing cannula second end 126 to puncture a access septum 163 configured to fluidly isolate fluid access 130 and portions of infusion device 100. In some examples, the technique includes causing a fluid flow from fluid reservoir 112 to cannula first end 124 using a fluid pump 127. The technique may include controlling an operation of fluid pump 127 using processing circuitry 114.

In examples, the technique includes electrically connecting a first connector 132 of first unit 106 and a second connector 136 of second unit 108 when second housing 116 engages first housing 110. First connector 132 may be in electrical communication with processing circuitry 114. Second connector 136 may be in electrical communication with processing circuitry 114. In examples, the technique includes establishing electrical connectivity between sensor 104 and processing circuitry 114 when first connector 132 electrically connects with second connector 136. The technique may include transmitting a signal indicative of a physiological characteristic of a user to processing circuitry 114 using the electrical connection between sensor 104 and the processing circuitry. In examples, the technique includes controlling an operation of fluid pump 127 using processing circuitry 114 based on the indicative signal.

The technique may include retracting first insertion needle 140 and second insertion needle 142 when second unit 108 is engaged with first unit 106. The technique may include retracting first insertion needle 140 and second insertion needle 142 in a direction away from first housing 110 (e.g., in the proximal direction P). In examples, the technique includes causing first insertion needle 140 to release cannula 102 when first insertion needle 140 retracts. The technique may include mechanically disengaging first insertion needle 140 from cannula 102 such that cannula first end 124 remains implanted in the user when first insertion needle 140 retracts. In examples, the technique includes causing second insertion needle 142 to release sensor 104 when second insertion needle 142 retracts. The technique may include mechanically disengaging second insertion needle 142 from sensor 104 such that at least some portion of sensor 104 remains implanted in the user when second insertion needle 142 retracts.

In examples, the technique includes positioning second unit 108 in an inserter 170. The technique may include moving second unit 108 toward first unit 106 using the inserter 170. In some examples, the technique includes causing inserter 170 to move second unit 108 toward first unit 106 by actuating a plunger 172. In examples, plunger 172 is configured to compress an insertion spring 186. The technique may include causing second unit 108 to move toward first unit 106 using an expansion of the insertion spring.

In examples, inserter 170 is configured to displace first insertion needle 140 over an axis A1 extending through first unit first channel 148 when second unit 108 moves toward first unit 106. In examples, inserter 170 is configured to displace second insertion needle 142 over an axis A2 extending through first unit second channel 154 when second unit 108 moves toward first unit 106. In examples, inserter 170 is configured to displace cannula second end 126 over an axis A3 extending through fluid access 130 when second unit 108 moves toward first unit 106. In examples, inserter 170 is configured to displace second connector 136 over an axis A4 extending through first connector 132 when second unit 108 moves toward first unit 106. In examples, the technique includes mating a serter member 174 of insertor 170 with first unit 106. The technique may include displacing first insertion needle 140 over axis A1, displacing second insertion needle 142 over axis A2, displacing cannula second end 126 over axis A3, and/or displacing second connector 136 over axis A4 when serter member 174 mates with first unit 106 using insertor 170.

In examples, the technique includes withdrawing first insertion needle 140 and second insertion needle 142 (e.g., in the proximal direction P) from first unit 106 and second unit 108 using insertor 170. The technique may include causing first insertion needle 140 and second insertion needle 142 to withdraw using an expansion of a withdrawal spring 194. In examples, the technique includes causing first insertion needle 140 to release cannula 102 and causing second insertion needle 142 to release sensor 104 by withdrawing first insertion needle 140 and second insertion needle 142. The technique may include withdrawing first insertion needle 140 and second insertion needle 142 by causing a needle carrier 156 to move in a direction away (e.g., in the proximal direction P) from first housing 110 and second housing 116.

The techniques and functionalities described in this disclosure, including those attributed to processor 143, processing circuitry, sensors, and/or various constituent components, may be implemented, at least in part, in hardware, software, firmware or any combination thereof. For example, various aspects of the techniques may be implemented within one or more processors, including one or more microprocessors, DSPs, ASICs, FPGAs, or any other equivalent integrated or discrete logic circuitry, as well as any combinations of such components, embodied in any suitable device. Processing circuitry, control circuitry, and sensing circuitry, as well as other processors, controllers, and sensors described herein, may be implemented at least in part as, or include, one or more executable applications, application modules, libraries, classes, methods, objects, routines, subroutines, firmware, and/or embedded code, for example. In addition, analog circuits, components and circuit elements may be employed to construct one, some or all of the control circuitry and sensors, instead of or in addition to the partially or wholly digital hardware and/or software described herein. Accordingly, analog or digital hardware may be employed, or a combination of the two.

In one or more examples, the techniques and functionalities described in this disclosure may be implemented in hardware, software, firmware, or any combination thereof. If implemented in software, the functions may be stored on, as one or more instructions or code, a computer-readable medium and executed by a hardware-based processing unit. The computer-readable medium may be an article of manufacture including a non-transitory computer-readable storage medium encoded with instructions. Instructions embedded or encoded in an article of manufacture including a non-transitory computer-readable storage medium encoded, may cause one or more programmable processors, or other processors, to implement one or more of the techniques described herein, such as when instructions included or encoded in the non-transitory computer-readable storage medium are executed by the one or more processors. Example non-transitory computer-readable storage media may include RAM, ROM, programmable ROM (PROM), erasable programmable ROM (EPROM), electronically erasable programmable ROM (EEPROM), flash memory, a hard disk, a compact disc ROM (CD-ROM), a floppy disk, a cassette, magnetic media, optical media, or any other computer readable storage devices or tangible computer readable media.

In some examples, a computer-readable storage medium comprises non-transitory medium. The term "non-transitory" may indicate that the storage medium is not embodied in a carrier wave or a propagated signal. In certain examples, a non-transitory storage medium may store data that can, over time, change (e.g., in RAM or cache).

The functionality described herein may be provided within dedicated hardware and/or software modules. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components. Also, the techniques could be fully implemented in one or more circuits or logic elements The present disclosure includes the following examples.

Example 1: An infusion device comprising: a first unit defining a first housing, wherein the first housing defines a first channel extending through the first housing, a second channel extending through the first housing, and a fluid access, wherein the first unit includes processing circuitry and a fluid reservoir in fluid communication with the fluid access; and a second unit defining a second housing configured to engage the first housing, the second unit comprising: a cannula having a first end and a second end; a sensor; a first insertion needle releasably carrying the cannula; and a second insertion needle releasably carrying the sensor, wherein: the first insertion needle is configured to insert the first end of the cannula through the first channel when the second housing engages the first housing, the second insertion needle is configured to insert the sensor through the second channel when the second housing engages the first housing, the second end of the cannula is configured to insert through the fluid access when the second housing engages the first housing, and the infusion device is configured to electrically connect the sensor and the processing circuitry when the second housing engages the first housing.

Example 2: The infusion device of example 1, wherein: the first insertion needle defines a first needle distal end configured to pierce the skin of a user, the second insertion needle defines a second needle distal end configured to pierce the skin of a user, the first insertion needle is configured to extend through the first channel and displace the first needle distal end away from the first housing to pierce the skin of the user when the second housing engages the first housing, and the second insertion needle is configured to extend through the second channel and translate the second needle distal end in a direction away from the first housing to pierce the skin of the user when the second housing engages with the first housing.

Example 3: The infusion device of example 1 or 2, wherein the second unit defines a second unit first channel extending through the second housing and a second unit second channel extending through the second housing, wherein the first insertion needle extends through the second unit first channel and the second insertion needle extends through the second unit first channel.

Example 4: The infusion device of any of examples 1-3, wherein the first insertion needle is configured to withdraw from the second unit first channel and the first channel of the first unit when the second housing is engaged with the first housing, and wherein the second insertion needle is configured to withdraw from the second unit second channel and the second channel of the first unit when the second housing is engaged with the first housing.

Example 5: The infusion device of any of examples 1-4, wherein the sensor is a glucose sensor and the cannula is configured to deliver insulin from the fluid reservoir when the second housing engages the first housing.

Example 6: The infusion device of any of examples 1-5, wherein the second unit is configured to withdraw the first end of the cannula from the first channel, withdraw the second end of the cannula from the fluid access, and withdraw the sensor from the second channel when the second housing is disengaged from the first housing.

Example 7: The infusion device of any of examples 1-6, wherein the second unit is configured to translate in a first direction to cause the second housing to engage the first housing, and wherein: the first insertion needle is configured to translate in the first direction to implant the first end of the cannula in a user when the second unit translates in the first direction, the second insertion needle is configured to translate in the first direction to implant the sensor in the user when the second unit translates in the first direction, the first insertion needle is configured to release the first end of the cannula when the first insertion needle translates in a second direction opposite the first direction, such that the first end of the cannula remains implanted in the user when the first insertion needle withdraws from the user, and the second insertion needle is configured to release the sensor when the first insertion needle translates in a second direction opposite the first direction, such that the first end of the cannula remains implanted in the user when the first insertion needle withdraws from the user.

Example 8: The infusion device of any of examples 1-7, wherein the cannula is configured to establish fluid communication from the first end of the cannula to the fluid reservoir when the second end of the cannula inserts through the fluid access.

Example 9: The infusion device of any of examples 1-8, wherein the first unit comprises an access septum configured to fluidly isolate the fluid reservoir and the second housing, wherein the second end of the cannula is configured to pierce the access septum when the second end of the cannula inserts through the fluid access.

Example 10: The infusion device of any of examples 1-9, wherein: the first insertion needle defines a first needle distal end configured to pierce the skin of a user, the second insertion needle defines a second needle distal end configured to pierce the skin of a user, and the infusion device is configured to cause the first needle distal end and the second needle distal end to pierce the skin of the user substantially concurrently.

Example 11: The infusion device of any of examples 1-10, wherein the first unit includes a first electrical contact in electrical communication with the processing circuitry, and wherein the second unit includes a second electrical contact in electrical communication with the sensor, and wherein the first electrical contact and the second electrical contact are configured to establish the electrical connection between the sensor and the processing circuitry when the second housing engages the first housing.

Example 12: The infusion device of any of examples 1-11, wherein the first unit further comprises a fluid pump configured to deliver a fluid from the fluid reservoir to the fluid access.

Example 13: The infusion device of any of examples 1-12, wherein the processing circuitry is configured to: receive a signal indicative of a physiological characteristic of the user from the sensor; and control an operation of the fluid pump based on the indicative signal.

Example 14: The infusion device of any of examples 1-13, further comprising an inserter configured to translate the second unit toward the first unit to cause the second housing to engage the first housing, wherein: the inserter is configured to mate with the first housing, the inserter is configured to align a first needle distal end of the first insertion needle with the first channel when the inserter is mated with the first housing, the inserter is configured to align a second needle distal end of the second insertion needle with the second channel when the inserter is mated with the first housing, and the inserter is configured to align the second end of the cannula with the fluid access when the inserter is mated with the first housing.

Example 15: The infusion device of any of examples 1-14, further comprising an inserter and a carrier attached to the first insertion needle and the second insertion needle, wherein: the inserter is configured to translate the second unit and the carrier in a first direction toward the first unit to cause the second housing to engage the first housing; and the inserter is configured to translate the carrier, the first insertion needle, and the second insertion needle away from the second housing in a second direction opposite the first direction when the second housing engages the first housing.

Example 16: An infusion device comprising: a first unit defining a first housing, wherein the first housing defines a first channel extending through the first housing, a second channel extending through the first housing, and a fluid access, and wherein the first unit includes processing circuitry, a fluid reservoir, and a fluid pump in fluid communication with the fluid access; and a second unit defining a second housing configured to engage the first housing, the second unit comprising: a cannula having a first end and a second end; and a sensor; a first insertion needle releasably carrying the cannula and configured to extend through the first channel; and a second insertion needle releasably carrying the sensor and configured to extend through the second channel, wherein: the first housing is configured to substantially secure the second housing from movement relative to the first housing when the second housing engages the first housing, the first insertion needle is configured to extend a portion of the cannula including the first end through the first channel when the first insertion needle extends through the first channel, the second insertion needle is configured to extend a portion of the sensor through the second channel when the second insertion needle extends through the second channel, the second end of the cannula is configured to insert through the fluid access when the second housing engages the first housing, wherein the cannula is configured to establish fluid communication from the first end of the cannula to the fluid reservoir when the second end of the cannula inserts through the fluid access, and the infusion device is configured to electrically connect the sensor and the processing circuitry when the second housing engages the first housing.

Example 17: The infusion device of example 16, further comprising an inserter, and wherein the second unit includes a carrier attached to the first insertion needle and the second insertion needle, wherein the inserter is configured to: releasably mate with the first housing, align the first needle distal end with the first channel when the inserter is releasably mated with the first housing, align the second needle distal end with the second channel when the inserter is releasably mated with the first housing, and align the second end of the cannula with the fluid access when the inserter is releasably mated with the first housing, and wherein the inserter is configured to translate the second unit in a first direction toward the first unit to cause the second housing to engage the first housing, and wherein the inserter is configured to translate the carrier, the first insertion needle, and the second insertion needle away from the second housing in a second direction opposite the first direction when the second housing is engaged with the first housing.

Example 18: The infusion device of example 16 or 17, wherein the processing circuitry is configured to: receive a signal indicative of a physiological characteristic of the user from the sensor; and control an operation of the fluid pump based on the indicative signal.

Example 19: A method comprising: engaging a first housing defined by a first unit and a second housing defined by a second unit, wherein the first unit includes processing circuitry and a fluid reservoir, and wherein the second unit includes a first insertion needle, a second insertion needle, a cannula, and a sensor; inserting, when the second housing engages the first housing, a first end of the cannula through a first channel defined by the first housing using the first insertion needle; inserting, when the second housing engages the first housing, the sensor through a second channel defined by the first housing using the second insertion needle; inserting, when the second housing engages the first housing, a second end of the cannula into a fluid access defined by the first housing; and electrically connecting, when the second housing engages the first housing, the sensor and the processing circuitry.

Example 20: The method of example 19, further comprising: translating the second unit in a first direction to engage the first housing and the second housing; and translating the first insertion needle and the second insertion needle in a second direction opposite the first direction when the first housing is engaged with the second direction.

Various examples have been described. These are other examples are within the scope of the disclosure.

What is claimed is:

1. An infusion device comprising:
   a first unit defining a first housing, wherein the first housing defines a first channel extending through the first housing, a second channel extending through the first housing, and a fluid access, wherein the first unit includes processing circuitry and a fluid reservoir in fluid communication with the fluid access; and
   a second unit defining a second housing configured to engage the first housing, the second unit comprising:
   a cannula having a first end and a second end;
   a sensor;
   a first insertion needle releasably carrying the cannula; and
   a second insertion needle releasably carrying the sensor, wherein:
      the first insertion needle is configured to insert the first end of the cannula through the first channel when the second housing engages the first housing,
      the second insertion needle is configured to insert the sensor through the second channel when the second housing engages the first housing,
      the second end of the cannula is configured to insert through the fluid access when the second housing engages the first housing, and
      the infusion device is configured to electrically connect the sensor and the processing circuitry when the second housing engages the first housing.

2. The infusion device of claim 1, wherein:
   the first insertion needle defines a first needle distal end configured to pierce the skin of a user,
   the second insertion needle defines a second needle distal end configured to pierce the skin of a user,
   the first insertion needle is configured to extend through the first channel and displace the first needle distal end away from the first housing to pierce the skin of the user when the second housing engages the first housing, and
   the second insertion needle is configured to extend through the second channel and translate the second needle distal end in a direction away from the first housing to pierce the skin of the user when the second housing engages with the first housing.

3. The infusion device of claim 1, wherein the second unit defines a second unit first channel extending through the second housing and a second unit second channel extending through the second housing, wherein the first insertion needle extends through the second unit first channel and the second insertion needle extends through the second unit first channel.

4. The infusion device of claim 3, wherein the first insertion needle is configured to withdraw from the second unit first channel and the first channel of the first unit when the second housing is engaged with the first housing, and wherein the second insertion needle is configured to withdraw from the second unit second channel and the second channel of the first unit when the second housing is engaged with the first housing.

5. The infusion device of claim 1, wherein the sensor is a glucose sensor and the cannula is configured to deliver insulin from the fluid reservoir when the second housing engages the first housing.

6. The infusion device of claim 1, wherein the second unit is configured to withdraw the first end of the cannula from the first channel, withdraw the second end of the cannula from the fluid access, and withdraw the sensor from the second channel when the second housing is disengaged from the first housing.

7. The infusion device of claim 1, wherein the second unit is configured to translate in a first direction to cause the second housing to engage the first housing, and wherein:
   the first insertion needle is configured to translate in the first direction to implant the first end of the cannula in a user when the second unit translates in the first direction,
   the second insertion needle is configured to translate in the first direction to implant the sensor in the user when the second unit translates in the first direction,
   the first insertion needle is configured to release the first end of the cannula when the first insertion needle translates in a second direction opposite the first direction, such that the first end of the cannula remains implanted in the user when the first insertion needle withdraws from the user, and
   the second insertion needle is configured to release the sensor when the second insertion needle translates in the second direction opposite the first direction, such that a first end of the sensor remains implanted in the user when the second insertion needle withdraws from the user.

8. The infusion device of claim 1, wherein the cannula is configured to establish fluid communication from the first end of the cannula to the fluid reservoir when the second end of the cannula inserts through the fluid access.

9. The infusion device of claim 1, wherein the first unit comprises an access septum configured to fluidly isolate the fluid reservoir and the second housing, wherein the second end of the cannula is configured to pierce the access septum when the second end of the cannula inserts through the fluid access.

10. The infusion device of claim 1, wherein:
the first insertion needle defines a first needle distal end configured to pierce the skin of a user,
the second insertion needle defines a second needle distal end configured to pierce the skin of a user, and
the infusion device is configured to cause the first needle distal end and the second needle distal end to pierce the skin of the user substantially concurrently.

11. The infusion device of claim 1, wherein the first unit includes a first electrical contact in electrical communication with the processing circuitry, and wherein the second unit includes a second electrical contact in electrical communication with the sensor, and wherein the first electrical contact and the second electrical contact are configured to establish the electrical connection between the sensor and the processing circuitry when the second housing engages the first housing.

12. The infusion device of claim 1, wherein the first unit further comprises a fluid pump configured to deliver a fluid from the fluid reservoir to the fluid access.

13. The infusion device of claim 12, wherein the processing circuitry is configured to:
receive a signal indicative of a physiological characteristic of user from the sensor; and
control an operation of the fluid pump based on the indicative signal.

14. The infusion device of claim 1 further comprising an inserter configured to translate the second unit toward the first unit to cause the second housing to engage the first housing, wherein:
the inserter is configured to mate with the first housing,
the inserter is configured to align a first needle distal end of the first insertion needle with the first channel when the inserter is mated with the first housing,
the inserter is configured to align a second needle distal end of the second insertion needle with the second channel when the inserter is mated with the first housing, and
the inserter is configured to align the second end of the cannula with the fluid access when the inserter is mated with the first housing.

15. The infusion device of claim 1 further comprising an inserter and a carrier attached to the first insertion needle and the second insertion needle, wherein:
the inserter is configured to translate the second unit and the carrier in a first direction toward the first unit to cause the second housing to engage the first housing; and
the inserter is configured to translate the carrier, the first insertion needle, and the second insertion needle away from the second housing in a second direction opposite the first direction when the second housing engages the first housing.

16. An infusion device comprising:
a first unit defining a first housing, wherein the first housing defines a first channel extending through the first housing, a second channel extending through the first housing, and a fluid access, and wherein the first unit includes processing circuitry, a fluid reservoir, and a fluid pump in fluid communication with the fluid access; and
a second unit defining a second housing configured to engage the first housing, the second unit comprising:
a cannula having a first end and a second end; and
a sensor;
a first insertion needle releasably carrying the cannula and configured to extend through the first channel; and
a second insertion needle releasably carrying the sensor and configured to extend through the second channel, wherein:
the first housing is configured to substantially secure the second housing from movement relative to the first housing when the second housing engages the first housing,
the first insertion needle is configured to extend a portion of the cannula including the first end through the first channel when the first insertion needle extends through the first channel,
the second insertion needle is configured to extend a portion of the sensor through the second channel when the second insertion needle extends through the second channel,
the second end of the cannula is configured to insert through the fluid access when the second housing engages the first housing, wherein the cannula is configured to establish fluid communication from the first end of the cannula to the fluid reservoir when the second end of the cannula inserts through the fluid access, and
the infusion device is configured to electrically connect the sensor and the processing circuitry when the second housing engages the first housing.

17. The infusion device of claim 16 further comprising an inserter, and wherein the second unit includes a carrier attached to the first insertion needle and the second insertion needle, wherein the inserter is configured to:
releasably mate with the first housing,
align a distal end of the first insertion needle with the first channel when the inserter is releasably mated with the first housing,
align a distal end of the second insertion needle with the second channel when the inserter is releasably mated with the first housing, and
align the second end of the cannula with the fluid access when the inserter is releasably mated with the first housing, and
wherein the inserter is configured to translate the second unit in a first direction toward the first unit to cause the second housing to engage the first housing, and
wherein the inserter is configured to translate the carrier, the first insertion needle, and the second insertion needle away from the second housing in a second direction opposite the first direction when the second housing is engaged with the first housing.

18. The infusion device of claim 16, wherein the processing circuitry is configured to:
receive a signal indicative of a physiological characteristic of a user from the sensor; and
control an operation of the fluid pump based on the indicative signal.

19. A method comprising:
engaging a first housing defined by a first unit and a second housing defined by a second unit, wherein the first unit includes processing circuitry and a fluid reservoir, and wherein the second unit includes a first insertion needle, a second insertion needle, a cannula, and a sensor;

inserting, when the second housing engages the first housing, a first end of the cannula through a first channel defined by the first housing using the first insertion needle;

inserting, when the second housing engages the first housing, the sensor through a second channel defined by the first housing using the second insertion needle;

inserting, when the second housing engages the first housing, a second end of the cannula into a fluid access defined by the first housing; and electrically connecting, when the second housing engages the first housing, the sensor and the processing circuitry.

20. The method of claim 19, further comprising:

translating the second unit in a first direction to engage the first housing and the second housing; and translating the first insertion needle and the second insertion needle in a second direction opposite the first direction when the first housing is engaged with the second housing.

\* \* \* \* \*

UNITED STATES PATENT AND TRADEMARK OFFICE
CERTIFICATE OF CORRECTION

PATENT NO. : 11,944,786 B2
APPLICATION NO. : 17/151385
DATED : April 2, 2024
INVENTOR(S) : Pananen et al.

It is certified that error appears in the above-identified patent and that said Letters Patent is hereby corrected as shown below:

In the Claims

In Column 37, in Claim 13, Line 33, delete "of user" and insert -- of a user --, therefor.

Signed and Sealed this
Fourteenth Day of May, 2024

Katherine Kelly Vidal
*Director of the United States Patent and Trademark Office*